United States Patent
Hoon et al.

(10) Patent No.: US 7,718,364 B2
(45) Date of Patent: May 18, 2010

(54) DNA MARKERS FOR MANAGEMENT OF CANCER

(75) Inventors: Dave S. B. Hoon, Los Angeles, CA (US); Bret Taback, 1431 Ocean Ave., Apt. #507, Santa Monica, CA (US) 90401

(73) Assignees: John Wayne Cancer Institute, Santa Monica, CA (US); Bret Taback, Santa Monica, CA (US)

( * ) Notice: Subject to any disclaimer, the term of this patent is extended or adjusted under 35 U.S.C. 154(b) by 866 days.

(21) Appl. No.: 10/809,965

(22) Filed: Mar. 25, 2004

(65) Prior Publication Data

US 2006/0051768 A1 Mar. 9, 2006

Related U.S. Application Data

(60) Provisional application No. 60/457,395, filed on Mar. 25, 2003.

(51) Int. Cl.
*C11Q 1/68* (2006.01)
*C07H 21/02* (2006.01)

(52) U.S. Cl. ........................ 435/6; 536/23.1

(58) Field of Classification Search .............. 435/6, 435/91.2; 536/23.1, 24.33
See application file for complete search history.

(56) References Cited

U.S. PATENT DOCUMENTS 6,465,177 B1 10/2002 Hoon ............................ 435/6
6,673,541 B1 * 1/2004 Klein et al. .................... 435/6

FOREIGN PATENT DOCUMENTS

WO WO 9629430 A1 * 9/1996
WO WO 00/17390 * 3/2000

OTHER PUBLICATIONS

Fujiwara et al. Plasma DNA microsatellites as tumor-specific markers and indicators of tumor progression in melanoma patients, Cancer Research, vol. 59, pp. 1567-1571, 1999.*

Anker et al. Detection of circulating tumor DNA in the blood (plasma/serum) of cancer patients, Cancer and Metastasis Reviews, vol. 18, pp. 65-73, 1999.*
Yang et al. Two-hit inactivation of FHIT by loss of heterozygosity and hypermethylation in breast cancer. Clinical Cancer Research, vol. 8, pp. 2890-2893, Sep. 2002.*
Kondo et al. Genetic instability and aberrant DNA methylation in chronic hepatitis and cirrhosis- a comprehensive study of loss of heterozygosity and microsatellite instability at 39 loci and DNA hypermethylation on 8CpG islands in microdissected specimens from patients with hepatocellular carcinoma, Hepatology, vol. 32, pp. 970-979, 2000.*
Locomte, T et al. Detection of free-circulating tumor=associated DNA in plasma of colorectal cancer patients and its association with prognosis. Int. J. Cancer, vol. 100, pp. 542-548, 2002.*
Bearzatto, A et al. p16INK4A hypermethylation detected by fluorescent methylation-specific PCR in plasmas from non-small cell lung cancer. Clin Cancer Res., vol. 8, pp. 3782-3787, 2002.*
Dominguez G et al. p14ARF promoter hypermethylation in plasma DNA as indicator of disease recurrence in bladder cancer patients. Clin Cancer Res., vol. 8, pp. 980-985, 2002.*
Silva JM et al. Persistence of tumor DNA in plasma of breast cancer patients after mastectomy. Annals of Surgical Oncology, vol. 9(1), pp. 71-76, 2002.*
Kawakami K et al. Hypermethylated APC DNA in plasma and prognosis of patients with esophageal adenocarcinoma. J National Cancer Institute, vol. 92, No. 22, 2000.*
Anker et al., Detection of circulating tumour DNA in the blood (plasma/serum) of cancer patients, Cancer and Metastasis Reviews, vol. 18, pp. 65-73, 1999.

* cited by examiner

*Primary Examiner*—Suryaprabha Chunduru
(74) *Attorney, Agent, or Firm*—Michael J. Wise; Perkins Coie LLP

(57) ABSTRACT

A method is provided for assessing allelic losses and hypermethylation of genes in CpG tumor promotor region on specific chromosomal regions in cancer patients, including melanoma, neuroblastoma breast, colorectal, and prostate cancer patients. The method relies on the evidence that free DNA and hypermethylation of genes in CpG tumor promotor region may be identified in the bone marrow, serum, plasma, and tumor tissue samples of cancer patients. Methods of melanoma, neuroblastoma, colorectal cancer, breast cancer and prostate cancer detection, staging, and prognosis are also provided.

19 Claims, 3 Drawing Sheets

SEQUENCE LISTING

```
<160> NUMBER OF SEQ ID NOS: 55

<210> SEQ ID NO 1
<211> LENGTH: 19
<212> TYPE: DNA
<213> ORGANISM: Artificial
<220> FEATURE:
<223> OTHER INFORMATION: Synthetic oligonucleotide

<400> SEQUENCE: 1
gaacgcgagc gattcgagt                                                  19

<210> SEQ ID NO 2
<211> LENGTH: 19
<212> TYPE: DNA
<213> ORGANISM: Artificial
<220> FEATURE:
<223> OTHER INFORMATION: Synthetic oligonucleotide

<400> SEQUENCE: 2
gaccaatcca accgaaacg                                                  19

<210> SEQ ID NO 3
<211> LENGTH: 21
<212> TYPE: DNA
<213> ORGANISM: Artificial
<220> FEATURE:
<223> OTHER INFORMATION: Synthetic oligonucleotide

<400> SEQUENCE: 3
ggattgggat gttgagaatg t                                               21
```

<210> SEQ ID NO 4
<211> LENGTH: 21
<212> TYPE: DNA
<213> ORGANISM: Artificial
<220> FEATURE:
<223> OTHER INFORMATION: Synthetic oligonucleotide

<400> SEQUENCE: 4
caaccaatcc aaccaaaaca a                                              21

<210> SEQ ID NO 5
<211> LENGTH: 22
<212> TYPE: DNA
<213> ORGANISM: Artificial
<220> FEATURE:
<223> OTHER INFORMATION: Synthetic oligonucleotide

<400> SEQUENCE: 5
ttaggttaga gggttatcgc gt                                             22

<210> SEQ ID NO 6
<211> LENGTH: 23
<212> TYPE: DNA
<213> ORGANISM: Artificial
<220> FEATURE:
<223> OTHER INFORMATION: Synthetic oligonucleotide

<400> SEQUENCE: 6
taactaaaaa ttcacctacc gac                                            23

<210> SEQ ID NO 7
<211> LENGTH: 25
<212> TYPE: DNA
<213> ORGANISM: Artificial
<220> FEATURE:
<223> OTHER INFORMATION: Synthetic oligonucleotide

<400> SEQUENCE: 7
taattttagg ttagagggtt attgt                                          25

<210> SEQ ID NO 8
<211> LENGTH: 20
<212> TYPE: DNA
<213> ORGANISM: Artificial
<220> FEATURE:
<223> OTHER INFORMATION: Synthetic oligonucleotide

<400> SEQUENCE: 8
cacaaccaat caacaacaca                                                20

<210> SEQ ID NO 9
<211> LENGTH: 18
<212> TYPE: DNA
<213> ORGANISM: Artificial
<220> FEATURE:
<223> OTHER INFORMATION: Synthetic oligonucleotide

<400> SEQUENCE: 9
tattgcggag tgcgggtc                                                  18

<210> SEQ ID NO 10
<211> LENGTH: 18
<212> TYPE: DNA
<213> ORGANISM: Artificial
<220> FEATURE:
<223> OTHER INFORMATION: Synthetic oligonucleotide

```
<400> SEQUENCE: 10
tcgacgaact cccgacga                                              18

<210> SEQ ID NO 11
<211> LENGTH: 24
<212> TYPE: DNA
<213> ORGANISM: Artificial
<220> FEATURE:
<223> OTHER INFORMATION: Synthetic oligonucleotide

<400> SEQUENCE: 11
gtgttttatt gtggagtgtg ggtt                                       24

<210> SEQ ID NO 12
<211> LENGTH: 21
<212> TYPE: DNA
<213> ORGANISM: Artificial
<220> FEATURE:
<223> OTHER INFORMATION: Synthetic oligonucleotide

<400> SEQUENCE: 12
ccaatcacaa actcccaaca a                                          21

<210> SEQ ID NO 13
<211> LENGTH: 20
<212> TYPE: DNA
<213> ORGANISM: Artificial
<220> FEATURE:
<223> OTHER INFORMATION: Synthetic oligonucleotide

<400> SEQUENCE: 13
gtgttaacgc gttgcgtatc                                            20

<210> SEQ ID NO 14
<211> LENGTH: 21
<212> TYPE: DNA
<213> ORGANISM: Artificial
<220> FEATURE:
<223> OTHER INFORMATION: Synthetic oligonucleotide

<400> SEQUENCE: 14
aaccccgcga actaaaaacg a                                          21

<210> SEQ ID NO 15
<211> LENGTH: 23
<212> TYPE: DNA
<213> ORGANISM: Artificial
<220> FEATURE:
<223> OTHER INFORMATION: Synthetic oligonucleotide

<400> SEQUENCE: 15
tttggttgga gtgtgttaat gtg                                        23

<210> SEQ ID NO 16
<211> LENGTH: 23
<212> TYPE: DNA
<213> ORGANISM: Artificial
<220> FEATURE:
<223> OTHER INFORMATION: Synthetic oligonucleotide

<400> SEQUENCE: 16
caaaccccac aaactaaaaa caa                                        23

<210> SEQ ID NO 17
```

```
<211> LENGTH: 20
<212> TYPE: DNA
<213> ORGANISM: Artificial
<220> FEATURE:
<223> OTHER INFORMATION: Synthetic oligonucleotide

<400> SEQUENCE: 17
ttcggggtgt agcggtcgtc                                                     20

<210> SEQ ID NO 18
<211> LENGTH: 22
<212> TYPE: DNA
<213> ORGANISM: Artificial
<220> FEATURE:
<223> OTHER INFORMATION: Synthetic oligonucleotide

<400> SEQUENCE: 18
gccccaatac taaatcacga cg                                                  22

<210> SEQ ID NO 19
<211> LENGTH: 24
<212> TYPE: DNA
<213> ORGANISM: Artificial
<220> FEATURE:
<223> OTHER INFORMATION: Synthetic oligonucleotide

<400> SEQUENCE: 19
gatgtttggg gtgtagtggt tgtt                                                24

<210> SEQ ID NO 20
<211> LENGTH: 24
<212> TYPE: DNA
<213> ORGANISM: Artificial
<220> FEATURE:
<223> OTHER INFORMATION: Synthetic oligonucleotide

<400> SEQUENCE: 20
ccaccccaat actaaatcac aaca                                                24

<210> SEQ ID NO 21
<211> LENGTH: 21
<212> TYPE: DNA
<213> ORGANISM: Artificial
<220> FEATURE:
<223> OTHER INFORMATION: Synthetic oligonucleotide

<400> SEQUENCE: 21
tttcggatgg ggttgttatc g                                                   21

<210> SEQ ID NO 22
<211> LENGTH: 20
<212> TYPE: DNA
<213> ORGANISM: Artificial
<220> FEATURE:
<223> OTHER INFORMATION: Synthetic oligonucleotide

<400> SEQUENCE: 22
gacgaacgcg aaacgatttc                                                     20

<210> SEQ ID NO 23
<211> LENGTH: 20
<212> TYPE: DNA
<213> ORGANISM: Artificial
<220> FEATURE:
<223> OTHER INFORMATION: Synthetic oligonucleotide

<400> SEQUENCE: 23
```

```
ttggatgggg ttgttattgt                                              20

<210> SEQ ID NO 24
<211> LENGTH: 20
<212> TYPE: DNA
<213> ORGANISM: Artificial
<220> FEATURE:
<223> OTHER INFORMATION: Synthetic oligonucleotide

<400> SEQUENCE: 24
accttcctcc aacaaacaca                                              20

<210> SEQ ID NO 25
<211> LENGTH: 28
<212> TYPE: DNA
<213> ORGANISM: Artificial
<220> FEATURE:
<223> OTHER INFORMATION: Synthetic oligonucleotide

<400> SEQUENCE: 25
gggttatttg gtaaattaag gtatagag                                     28

<210> SEQ ID NO 26
<211> LENGTH: 28
<212> TYPE: DNA
<213> ORGANISM: Artificial
<220> FEATURE:
<223> OTHER INFORMATION: Synthetic oligonucleotide

<400> SEQUENCE: 26
cacctaaaaa taaaacaaaa actaccac                                     28

<210> SEQ ID NO 27
<211> LENGTH: 23
<212> TYPE: DNA
<213> ORGANISM: Artificial
<220> FEATURE:
<223> OTHER INFORMATION: Synthetic oligonucleotide

<400> SEQUENCE: 27
gggagtttga gtttattgag ttg                                          23

<210> SEQ ID NO 28
<211> LENGTH: 25
<212> TYPE: DNA
<213> ORGANISM: Artificial
<220> FEATURE:
<223> OTHER INFORMATION: Synthetic oligonucleotide

<400> SEQUENCE: 28
ctctactcat ctataaccca aatac                                        25

<210> SEQ ID NO 29
<211> LENGTH: 30
<212> TYPE: DNA
<213> ORGANISM: Artificial
<220> FEATURE:
<223> OTHER INFORMATION: Synthetic oligonucleotide

<400> SEQUENCE: 29
gtgtgataga agtagtagga agtgagttgt                                   30

<210> SEQ ID NO 30
<211> LENGTH: 29
<212> TYPE: DNA
```

```
<213> ORGANISM: Artificial
<220> FEATURE:
<223> OTHER INFORMATION: Synthetic oligonucleotide

<400> SEQUENCE: 30
actccatcaa actctacccc tttttaac                                              29

<210> SEQ ID NO 31
<211> LENGTH: 19
<212> TYPE: DNA
<213> ORGANISM: Artificial
<220> FEATURE:
<223> OTHER INFORMATION: Synthetic oligonucleotide

<400> SEQUENCE: 31
gttgtyggag gattagggt                                                        19

<210> SEQ ID NO 32
<211> LENGTH: 21
<212> TYPE: DNA
<213> ORGANISM: Artificial
<220> FEATURE:
<223> OTHER INFORMATION: Synthetic oligonucleotide

<400> SEQUENCE: 32
taccccttaa ctacccctttc c                                                    21

<210> SEQ ID NO 33
<211> LENGTH: 29
<212> TYPE: DNA
<213> ORGANISM: Artificial
<220> FEATURE:
<223> OTHER INFORMATION: Synthetic oligonucleotide

<400> SEQUENCE: 33
aatcataaat tataacaaac aaaccaact                                             29

<210> SEQ ID NO 34
<211> LENGTH: 28
<212> TYPE: DNA
<213> ORGANISM: Artificial
<220> FEATURE:
<223> OTHER INFORMATION: Synthetic oligonucleotide

<400> SEQUENCE: 34
cgtttcgtta ttttttgttt tcggtttc                                              28

<210> SEQ ID NO 35
<211> LENGTH: 17
<212> TYPE: DNA
<213> ORGANISM: Artificial
<220> FEATURE:
<223> OTHER INFORMATION: Synthetic oligonucleotide

<400> SEQUENCE: 35
ccgaaaaccc cgcctcg                                                          17

<210> SEQ ID NO 36
<211> LENGTH: 31
<212> TYPE: DNA
<213> ORGANISM: Artificial
<220> FEATURE:
<223> OTHER INFORMATION: Synthetic oligonucleotide

<400> SEQUENCE: 36
ttttgttttg ttattttttg tttttggttt t                                          31
```

<210> SEQ ID NO 37
<211> LENGTH: 20
<212> TYPE: DNA
<213> ORGANISM: Artificial
<220> FEATURE:
<223> OTHER INFORMATION: Synthetic oligonucleotide

<400> SEQUENCE: 37
cccccaaaaa ccccacctca                                             20

<210> SEQ ID NO 38
<211> LENGTH: 23
<212> TYPE: DNA
<213> ORGANISM: Artificial
<220> FEATURE:
<223> OTHER INFORMATION: Synthetic oligonucleotide

<400> SEQUENCE: 38
tttcgacgtt cgtaggtttt cgc                                         23

<210> SEQ ID NO 39
<211> LENGTH: 22
<212> TYPE: DNA
<213> ORGANISM: Artificial
<220> FEATURE:
<223> OTHER INFORMATION: Synthetic oligonucleotide

<400> SEQUENCE: 39
gcactcttcc gaaaacgaaa cg                                          22

<210> SEQ ID NO 40
<211> LENGTH: 29
<212> TYPE: DNA
<213> ORGANISM: Artificial
<220> FEATURE:
<223> OTHER INFORMATION: Synthetic oligonucleotide

<400> SEQUENCE: 40
tttgtgtttt gatgtttgta ggtttttgt                                   29

<210> SEQ ID NO 41
<211> LENGTH: 27
<212> TYPE: DNA
<213> ORGANISM: Artificial
<220> FEATURE:
<223> OTHER INFORMATION: Synthetic oligonucleotide

<400> SEQUENCE: 41
aactccacac tcttccaaaa acaaaac                                     27

<210> SEQ ID NO 42
<211> LENGTH: 24
<212> TYPE: DNA
<213> ORGANISM: Artificial
<220> FEATURE:
<223> OTHER INFORMATION: Synthetic oligonucleotide

<400> SEQUENCE: 42
ggatagtcgg atcgagttaa cgtc                                        24

<210> SEQ ID NO 43
<211> LENGTH: 16
<212> TYPE: DNA
<213> ORGANISM: Artificial
<220> FEATURE:

```
<223> OTHER INFORMATION: Synthetic oligonucleotide

<400> SEQUENCE: 43
ccctcccaaa cgccga                                                        16

<210> SEQ ID NO 44
<211> LENGTH: 27
<212> TYPE: DNA
<213> ORGANISM: Artificial
<220> FEATURE:
<223> OTHER INFORMATION: Synthetic oligonucleotide

<400> SEQUENCE: 44
ggaggatagt tggattgagt taatgtt                                            27

<210> SEQ ID NO 45
<211> LENGTH: 21
<212> TYPE: DNA
<213> ORGANISM: Artificial
<220> FEATURE:
<223> OTHER INFORMATION: Synthetic oligonucleotide

<400> SEQUENCE: 45
caaatccctc ccaaacacca a                                                  21

<210> SEQ ID NO 46
<211> LENGTH: 24
<212> TYPE: DNA
<213> ORGANISM: Artificial
<220> FEATURE:
<223> OTHER INFORMATION: Synthetic oligonucleotide

<400> SEQUENCE: 46
ttattagagg gtggggcgga tcgc                                               24

<210> SEQ ID NO 47
<211> LENGTH: 20
<212> TYPE: DNA
<213> ORGANISM: Artificial
<220> FEATURE:
<223> OTHER INFORMATION: Synthetic oligonucleotide

<400> SEQUENCE: 47
gacccgaacc gcgaccgtaa                                                    20

<210> SEQ ID NO 48
<211> LENGTH: 24
<212> TYPE: DNA
<213> ORGANISM: Artificial
<220> FEATURE:
<223> OTHER INFORMATION: Synthetic oligonucleotide

<400> SEQUENCE: 48
ttattagagg gtggggtgga ttgt                                               24

<210> SEQ ID NO 49
<211> LENGTH: 22
<212> TYPE: DNA
<213> ORGANISM: Artificial
<220> FEATURE:
<223> OTHER INFORMATION: Synthetic oligonucleotide

<400> SEQUENCE: 49
caaccccaaa ccacaaccat aa                                                 22
```

```
<210> SEQ ID NO 50
<211> LENGTH: 23
<212> TYPE: DNA
<213> ORGANISM: Artificial
<220> FEATURE:
<223> OTHER INFORMATION: Synthetic oligonucleotide

<400> SEQUENCE: 50
ccaactccaa atcccctctc tat                                          23

<210> SEQ ID NO 51
<211> LENGTH: 30
<212> TYPE: DNA
<213> ORGANISM: Artificial
<220> FEATURE:
<223> OTHER INFORMATION: Synthetic oligonucleotide

<400> SEQUENCE: 51
tgattaattt agattgggtt tagagaagga                                   30

<210> SEQ ID NO 52
<211> LENGTH: 26
<212> TYPE: DNA
<213> ORGANISM: Artificial
<220> FEATURE:
<223> OTHER INFORMATION: Synthetic oligonucleotide

<400> SEQUENCE: 52
cccttcctat tcctaaatcc aaccta                                       26

<210> SEQ ID NO 53
<211> LENGTH: 26
<212> TYPE: DNA
<213> ORGANISM: Artificial
<220> FEATURE:
<223> OTHER INFORMATION: Synthetic oligonucleotide

<400> SEQUENCE: 53
cgtttgcgat ttggtgagtg tttggg                                       26

<210> SEQ ID NO 54
<211> LENGTH: 33
<212> TYPE: DNA
<213> ORGANISM: Artificial
<220> FEATURE:
<223> OTHER INFORMATION: Synthetic oligonucleotide

<400> SEQUENCE: 54
caactaccgt ataaaattac acgcgatacc ccg                               33

<210> SEQ ID NO 55
<211> LENGTH: 26
<212> TYPE: DNA
<213> ORGANISM: Artificial
<220> FEATURE:
<223> OTHER INFORMATION: Synthetic oligonucleotide

<400> SEQUENCE: 55
ccgaatacgt tccgaatcct accccg                                       26
```

US 7,718,364 B2

DNA MARKERS FOR MANAGEMENT OF CANCER

RELATED APPLICATION

This application claims priority to U.S. Provisional Application Ser. No. 60/457,395, filed Mar. 25, 2003, the content of which is incorporated herein by reference.

This invention was made with support in part by grants from NCI (Grant Nos. R21 CA100314, PO CA 29605 Project II, and PO CA 13917 Project II), Gonda Foundation, USA DOD Breast Cancer Research Grant, California Breast Cancer Research Grant, and Roy E Coates Foundation. Therefore, the U.S. government has certain rights in the invention.

FIELD OF THE INVENTION

The present invention is related to the fields of molecular biology and oncology and provides methods for diagnosis, staging and monitoring of cancer patients.

BACKGROUND OF THE INVENTION

Bone Marrow is the most frequent site of the systemic spread of some types of cancer, including breast[1,2] neuroblastoma, colorectal, and prostate cancer. Once metastases are clinically apparent, overall prognosis is poor. Undetected occult tumor cells contribute to disease recurrence and therefore methods to identify subclinical disease (micrometastasis) may improve staging and guide additional therapeutic decisions. Historically, conventional cytologic assessment of blood and bone marrow (BM) aspirates has been performed with limited success[3,4]. Immunocytochemical techniques using antibodies specific to epithelial antigens have improved sensitivity and can identifying a single tumor cell amongst a background of >1 million normal cells[5,6]. Enrichment methods with antibody-magnetic bead conjugates of BM aspirates have demonstrated the presence of occult tumor cells in early stage breast cancer patients[5,7].

Recently it has been shown that the detection of micrometastasis in the BM of early stage breast cancer patients is an independent prognostic risk factor[8,9]. However, the accurate microscopic analysis of many cytologic samples requires considerable cytopathologic expertise and can be tedious, particularly if performed serially to assess disease progression and/or response to treatment. Additionally, the variable specificity of individual antibodies used to detect single cells has been questioned[8,10,11]. Finally, these assay systems cannot characterize the biologic behavior of the cells being detected and thus many may represent dormant tumor cells, apoptotic cells, nonpathologic tumor cells, or displaced normal breast epithelial cells.

A variety of serial genetic changes have been implicated in the initiation and progression of solid tumors. One such event, allelic imbalance (loss of heterozygosity; LOH) has been shown to occur commonly in primary breast tumors and with additional frequency in metastasis[12-15]. Furthermore, there is emerging evidence to suggest that microsatellite markers for detecting LOH at specific chromosome loci may have important clinical prognostic correlations[12,16,17]. However, the examination of an excised primary tumor specimen may be of limited value in that it provides information of those genetic events that have occurred and not ongoing alterations which may be of clinical relevance, either prognostically or for therapeutic decisions. Additionally, because of the potentially long latent period that may exist between early breast cancer diagnosis and clinically detectable systemic recurrence, improved assessment methods are needed for serial surveillance of occult disease progression and monitoring response to therapy.

Recently it has been shown that free tumor-associated DNA can be identified in the serum and plasma from patients with melanoma, breast, lung, renal, gastrointestinal, and head and neck tumors[18-32]. Furthermore a high-quality concordance has been shown to exist between the genetic alterations (i.e., LOH, microsatellite instability, mutations) found in circulating tumor DNA and those from the primary tumor suggesting a potential surrogate tumor marker[20-22,27,28]. Early studies have shown the prognostic importance of circulating microsatellite markers for LOH in blood[21,24]. Although, BM is a common site for recurrence of some types of cancer, such as breast and prostate cancer, to date, BM has not been studied for the presence of suitable genetic markers.

Recently, methylation of gene promoter regions and the role that this epigenetic event plays in the development of various cancers has become an important area of investigation in assessing the mechanisms of tumor suppressor and regulatory gene inactivation. The tumor suppressor genes (TSG) can be transcriptionally silenced when their promoter region CpG islands contain methylated cytosines located 5' to an adjacent guanine. The utilization of methylation-specific PCR (MSP) assay has simplified and significantly improved detecting hypermethylated CpG bases with minimum amount of DNA. The methylation status of several TSG promoter regions have been profiled for a number of cancers. The hypermethylation of CpG islands of promoter regions of TSG is quite common and is a significant genetic aberration for tumor cells to shut off TSG expression.

Majority of these studies have been focused on carcinomas; there are limited studies in cutaneous melanomas and other types of cancers. The studies of epigenetic inactivation of TSG in melanomas have been limited mostly to methylation of promoter regions of $p16^{INK4a}$ and MGMT ($O^6$-methylguanine-DNA methyltransferase). Interestingly, the frequency of TSG inactivation or mutations in oncogenes is reportedly low in cutaneous melanomas. These observations have been a major enigma in deciphering the genetic events occurring in melanoma progression.

SUMMARY OF THE INVENTION

The present invention is based on the unexpected discovery that DNA markers can be detected in cell-free bone marrow samples and are useful for cancer diagnosis, staging, and prognosis.

Accordingly, the invention features a method of detecting DNA markers in a sample, comprising providing a cell-free bone marrow sample from a subject and detecting one or more DNA markers in the sample. Examples of DNA markers include those in the 1p, 3p, 6p, 6q, 8p, 10q, 11q, 14q, 16q, or 17p region. In particular, the DNA markers may be indicative of LOH, DNA hypermethylation, or DNA mutation. Such DNA markers include D1S228, D8S321, D4S175, D4S1586, D5S299, D8S133, D8S261, D8S262, D8S264, D9S171, D10S197, D10S591, D10S532, D14S51, D14S62, D15S127, D16S421, D16S422, D17S796, D17S849, D17S855, D18S58, D18S61, and D18S70; those indicative of hypermethylation in RASSF1A, MGMT, GSTP1, RAR-β, TWIST, APC, DAPK, P16, or Cyclin D2 promoter; and those indicative of mutation in KRAS and BRAF gene (e.g. mutation at codon 12 of KRAS and BRAF K600E mutation).

In one aspect, the invention provides a method of detecting cancer, comprising providing a cell-free bone marrow sample from a subject and detecting one or more DNA markers in the sample, wherein LOH, hypermethylation, or mutation of the markers is indicative of cancer (e.g., melanoma, neuroblastoma, colorectal, breast, or prostate cancer) in the subject.

In another aspect, the invention provides a method of staging cancer, comprising providing a cell-free bone marrow sample from a subject suffering from cancer and detecting one or more DNA markers in the sample, wherein LOH, hypermethylation, or motation of the markers is indicative of an advanced stage of the cancer in the subject.

The invention further provides a method of prognosing cancer, comprising providing a cell-free bone marrow sample from a subject suffering from cancer and detecting one or more DNA markers in the sample, wherein LOH, hypermethylation, or mutation of the markers is indicative of a poor prognosis of the cancer in the subject.

The invention is also based on the unexpected discovery that LOH and hypermethylation of DNA markers, when combined, provide more sensitive and precise diagnosis, staging and prognosis of cancer than when used individually. Therefore, the invention provides a method of detecting LOH and DNA hypermethylation, comprising providing a sample from a subject and detecting a combination of LOH and DNA hypermethylation in the sample (e.g., a serum, plasma or tissue sample). In one embodiment, the LOH is detected through DNA markers including D1S228, D8S321, D4S175, D4S1586, D5S299, D8S133, D8S261, D8S262, D8S264, D9S171, D10S197, D10S591, D10S532, D14S51, D14S62, D15S127, D16S421, D16S422, D17S796, D17S849, D17S855, D18S58, D18S61, or D18S70. In another embodiment, the DNA hypermethylation is detected in RASSF1A, MGMT, GSTP1, RAR-β, TWIST, APC, DAPK, P16, KRAS, BRAF, or Cyclin D2 promoter.

In one aspect, the invention features method of detecting cancer, comprising providing a sample from a subject and detecting one or more DNA markers in the sample, wherein a combination of LOH and hypermethylation of the markers is indicative of cancer (e.g., melanoma, neuroblastoma, colorectal, breast, or prostate cancer) in the subject.

In another aspect, the invention features a method of staging cancer, comprising providing a sample from a subject suffering from cancer and detecting one or more DNA markers in the sample, wherein a combination of LOH and hypermethylation of the markers is indicative of an advanced stage of the cancer in the subject.

In still another aspect, the invention features a method of prognosing cancer, comprising providing a sample from a subject suffering from cancer and detecting one or more DNA markers in the sample, wherein a combination of LOH and hypermethylation of the markers is indicative of a poor prognosis of the cancer in the subject.

Moreover, the invention provides kits and packaged products for implementing the methods described above. For example, one packaged product comprises a container, one or more agents for detecting one or more DNA markers in a sample and an insert associated with the container and indicating that the sample is a cell-free bone marrow sample.

Another example of a packaged product comprises a container, one or more agents for detecting one or more DNA markers in a cell-free bone marrow sample from a subject, and an insert associated with the container and indicating that LOH, hypermethylation, or mutation of the markers is indicative of cancer in the subject.

A packaged product may also comprise a container, one or more agents for detecting one or more DNA markers in a cell-free bone marrow sample from a subject suffering from cancer, and an insert associated with the container and indicating that LOH, hypermethylation, or mutation of the markers is indicative of an advanced stage of the cancer or a poor prognosis of the cancer in the subject.

The invention further provides (1) a kit comprising one or more agents for detecting a combination of LOH and DNA hypermethylation of one or more DNA markers in a sample; (2) a packaged product, comprising a container, one or more agents for detecting one or more DNA markers in a sample from a subject and an insert associated with the container and indicating that a combination of LOH and hypermethylation of the markers is indicative of cancer in the subject; and (3) a packaged product, comprising a container, one or more agents for detecting one or more DNA markers in a sample from a subject suffering from cancer, and an insert associated with the container and indicating that a combination of LOH and hypermethylation of the markers is indicative of an advanced stage of the cancer or a poor prognosis of the cancer in the subject.

The methods of the present invention advantageously permit a minimally invasive detection of tumor genetic changes that may provide valuable prognostic and diagnostic information, which may improve staging of the disease and monitoring of disease progression and response to therapy. In addition, because the methods of the present invention may be used to survey ongoing genetic changes, they may also be used to identify potential targets to individualize patient therapy. The method may also be used to identify markers in BM aspirates, plasma, and serum for other types of cancers.

The above-mentioned and other features of this invention and the manner of obtaining and using them will become more apparent, and will be best understood, by reference to the following description, taken in conjunction with the accompanying drawings. These drawings depict only typical embodiments of the invention and do not therefore limit its scope.

Also shown are representative examples of tumor histopathology negative patients' paraffin-embedded lymph nodes (PLN) analyzed by CAE for determining methylation status of (D) RAR-β2, (E) MGMT, and (F) RASSF1A.

Figure 2:
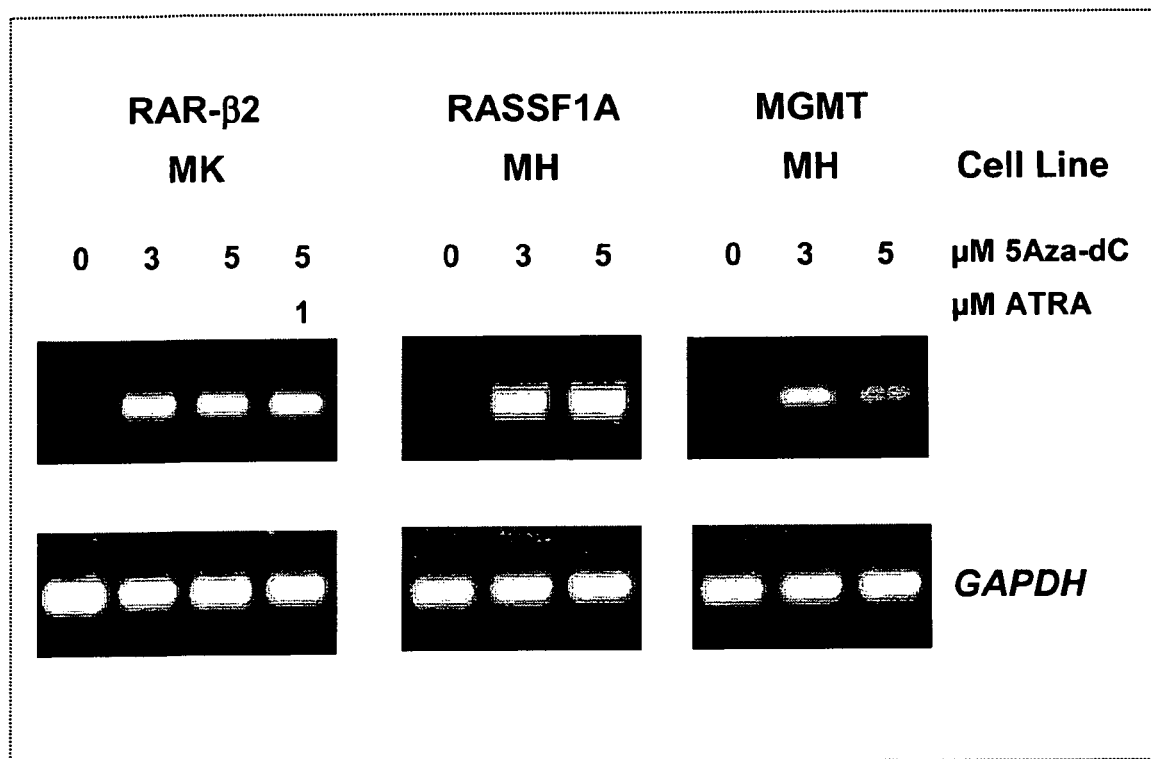

FIG. 2 shows representative expression and re-expression of RAR-β2, RASSF1A and MGMT in two melanoma cell lines treated with 5 Aza-dC. The cells were treated for four days with different concentrations of 5 Aza-dC followed by 24 h treatment with ATRA where indicated. Gene expression was analyzed by RT-PCR. The house-keeping gene GAPDH was included as an RT-PCR control for all assays.

Figure 3:
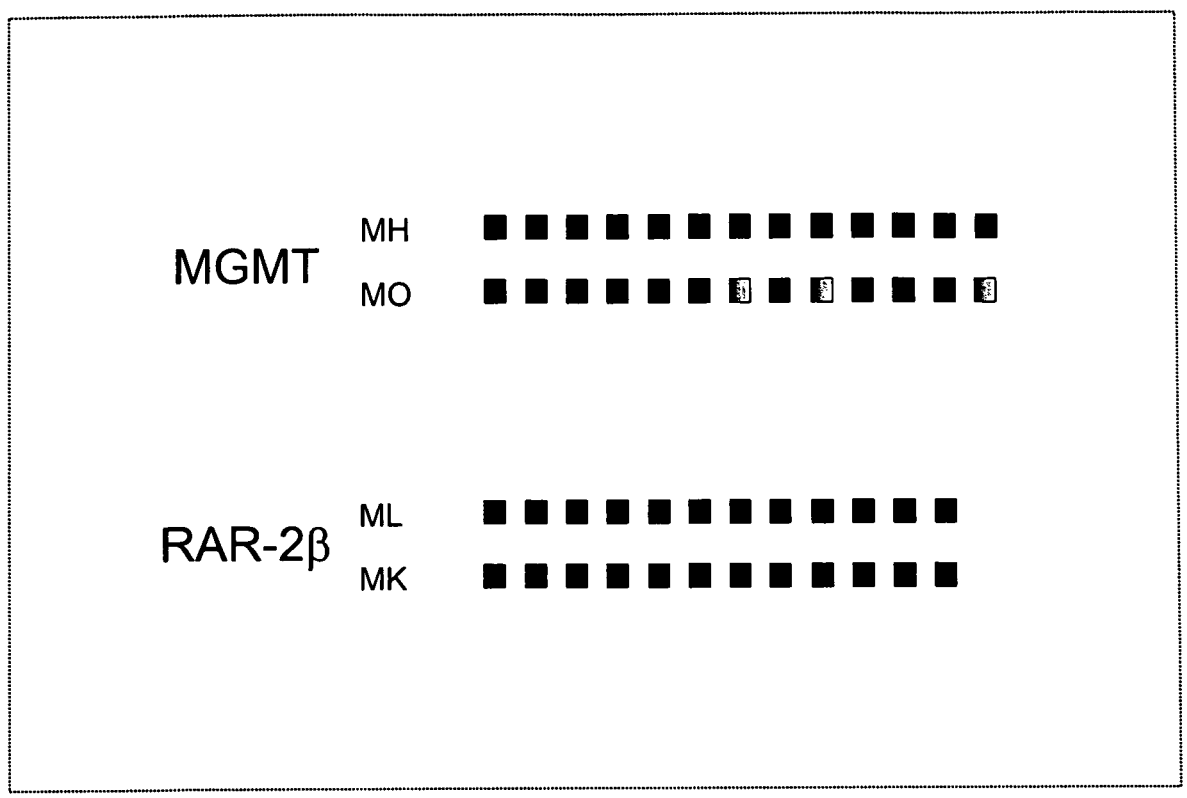

FIG. 3 shows representative PCR analysis of promoter region CpG island sequence of MGMT and RAR-β2 from bisulfite-treated DNA obtained from melanoma cell lines. Fully methylated CpGs are indicated as solid black boxes and partially methylated CpGs are shown as shaded boxes. All CpGs contained in the MSP products are shown.

Figure 4:
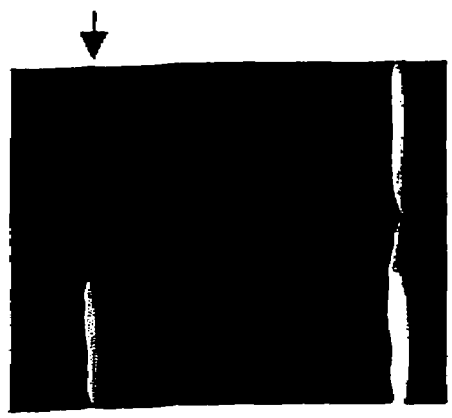
Figure 4:
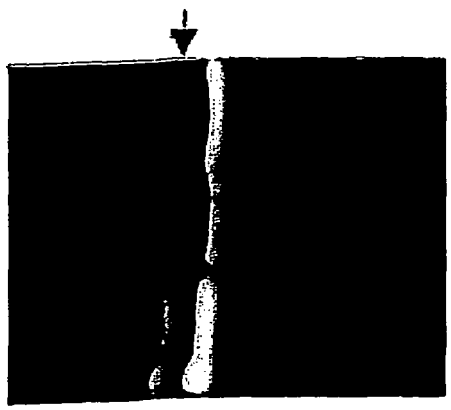
Figure 4:
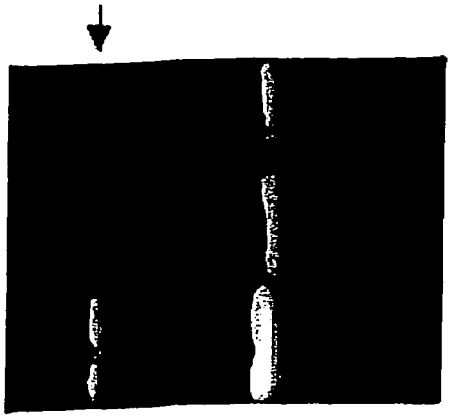

FIG. 4 provides representative images demonstrating LOH in breast cancer patients' paired BM aspirate (BM) and primary tumors (T) at D14S62, D14S51, and D8S321, respectively. Allelic loss is represented by the arrows. The first lane of each panel exhibits patients' lymphocyte DNA (L) allele pattern as a control.

DETAILED DESCRIPTION OF THE INVENTION

Since BM is a common site for cancer recurrence in certain types of cancer and because an application of conventional histochemical techniques to BM has been limited due to sub-optimal efficiency and sensitivity, it is one object of the present invention to determine whether BM aspirates may be used as a source of tumor-specific DNA associated with systemic metastasis from cancer, including metastasis associated with neuroblastoma, breast, prostate, and colorectal cancer. It is a further object of the present invention to identify tumor-specific nucleic acid alterations in the bone marrow, serum/plasma, and tumor tissue samples of cancer patients as diagnostic and prognostic markers of malignancy. Also, since the hypermethylation of CpG islands of promoter regions of TSG appears to play a significant role in the development of various cancers, it is another objective of the present invention to identify TSG and tumor-related genes methylation of which could indicate development of a cancer. It is a further object of the present invention to develop a method of using the identified methylation markers in the bone marrow, serum/plasma, and tumor tissue samples of cancer patients to diagnose malignancy.

It is a discovery of the present invention that LOH may be detected in BM aspirates and that the advancement of AJCC stages is associated with an increased incidence of LOH. In one study, the inventors used a panel of microsatellite markers for LOH on chromosomes 1p, 3p, 6p, 6q, 8p, 10q, 11q, 14q, 16q, and 17p to demonstrate the association between the LOH identified in BM aspirates with stage and tumor type in breast cancer. The inventors believe that other cancers that metastasize preferentially in bone, such as melanoma, prostate, and colorectal cancers, may be detected and monitored using the same group of LOH markers that were identified in breast cancer patients.

In another study, the inventors have demonstrated a correlation of LOH identified in serum/plasma of prostate cancer patients and AJCC staging. In still another study, the inventors showed that the presence of certain circulating nucleic acids in serum/plasma may assist in diagnosis of colorectal cancer. Accordingly, the present invention provides tumor-related genetic markers in BM aspirates, serum/plasma, and tumor tissue samples of cancer patients and provides a unique approach for assessing the subclinical systemic disease progression and the monitoring of cancer patients. The present invention also provides molecular techniques for the identification of genetic alterations on circulating nucleic acids in the bone marrow aspirates, plasma, serum, and tumor tissue of cancer patients.

One aspect of the present invention provides a detection assay for detecting the loss of heterozygosity (LOH) in DNA from BM, tumor tissue, plasma, and serum. The assay comprises the steps of (a) amplifying nucleic acid from an LOH marker, if present, (b) detecting the presence or absence of the LOH marker, and (c) correlating the findings with the occurrence and/or progression of a cancer. The determination of heterozygosity is well within the skill of the art and includes examining the second sample of DNA, which is isolated from non-neoplastic tissue. For example, U.S. Pat. No. 6,465,177, which is assigned to the assignee of the present invention and the content of which is incorporated herein by the reference, describes the detection of the loss of heterozygosity in the tumor and serum of melanoma patients.

Although any detection method may be used in association with markers of the present invention, in one embodiment amplification/detection methods used were PCR-based methods selected from the group consisting of PCR and gel electrophoresis using labeled primers (fluorescent or radioactive), RealTime PCR using specific labeled primers Taqman and probes (labeled with chromatographic dyes), and capillary array electrophoresis (CAE) with labeled PCR primers (no probes).

In one embodiment, the detection is carried out in a sample derived from bone marrow aspirates, plasma/serum, or tumor tissues. In another embodiment, because the combination of assessing blood, tumor tissue, and bone marrow is believed by the inventors to have a better predictive and diagnostic value, LOH is assessed in several different samples selected from the group consisting of BM aspirates, tumor tissue, serum, and plasma.

In one embodiment of the present invention, the set of alleles which are tested for LOH in BM aspirate, blood/plasma, or tumor tissue sample are selected from the group consisting of D1S228, D8S321, D4S175, D4S1586, D5S299, D8S133, D8S261, D8S262, D8S264, D9S171, D10S197, D10S591, D10S532, D14S51, D14S62, D15S127, D16S421, D16S422, D17S796, D17S849, D17S855, D18S58, D18S61, and D18S70.

It is also a discovery of the present invention that the methylation of DNA CpG tumor promoter regions is detectable in the plasma/serum, tumor tissue, and bone marrow of breast melanoma colon cancer patients for the following genes: RASSF1A, MGMT, GSTP1, RAR-β, TWIST, APC, DAPK, P16, and Cyclin D2 (CCND2). For example, although there are no reported comprehensive studies on melanoma tumor methylation correlating with clinicopathology, the inventors discovered an inactivation of a newly identified TSGs RASSF1A and RAR-β in melanomas, as well as methylation of MGMT.

The inventors believe that methylation markers may be used to provide significant prognostic and diagnostic information in cancer patients, including melanoma, colorectal, breast, and prostate cancer patients. The inventors also believe that utilization of both LOH markers and DNA methylation markers will allow establishing a comprehensive panel of human genetic prognostic molecular markers (PMMs) for melanoma, colorectal, breast, and prostate cancer. Primary tumors, metastatic tissue, blood (plasma/serum) or/and BM may be tested for methylation and microsatellite DNA markers for diagnosis and prognosis. For example, blood (plasma/serum) and BM LOH markers may be used as PMM in patient follow up to identify sub-clinical disease recurrence. Assessment of tumor tissue may be used for prognosis of disease outcome. Although it appears that LOH and methylation markers somewhat overlap for breast, prostate, melanoma and colon cancer, there are specific LOH and methylation markers that are more frequent or exclusively in specific cancers. Thus, in one embodiment, a panel of markers specific to the cancer suspected in the patient is used. In another embodiment, a panel comprising a broad range markers, including non-specific markers, is used to conduct a broader screening for various types of cancer.

In another aspect of the present invention, BM aspirates, blood, and tumor are assessed collectively for LOH and methylation markers to obtain a comprehensive profile of cancer patients, including prediction of metastasis to lymph nodes and disease outcome. The obtained results may be used to predict metastasis to lymph nodes (sentinel node) and disease outcome in cancer patients, including breast cancer, prostate cancer, and melanoma patients.

For example, in one embodiment, BM aspirates, serum, and/or plasma samples are evaluated for the presence of microsatellite markers selected from the group consisting of D1S228, D8S321, D4S175, D4S1586, D5S299, D8S133, D8S261, D8S262, D8S264, D9S171, D10S197, D10S591, D10S532, D14S51, D14S62, D15S127, D16S421, D16S422, D17S796, D17S849, D17S855, D18S58, D18S61, and D18S70 and methylation markers selected from the group consisting of RASSF1A, MGMT, GSTP1, RAR-β, TWIST, APC, DAPK, P16, and Cyclin D2 (CCND2) to obtain a prognostic and diagnostic information in cancer patients, including melanoma, breast, colorectal, and prostate cancer patients. In another embodiment, BM aspirates, serum, and/or plasma samples are evaluated for the presence of microsatellite markers with LOH on chromosomes 1p, 3p, 6p, 6q, 9p, 10q, 11q, and 12q and methylation markers RASSF1A, MGMT, and RAR-β to obtain prognostic and diagnostic information in breast cancer patients.

There is mounting evidence to suggest that the presence of occult tumor cells in the BM of breast cancer patients may have prognostic significance[9,33-38]. Furthermore, some have shown these findings to be independent of pathologic lymph node status[8,9]. These studies are important because, historically, 20% of lymph node negative patients will subsequently develop systemic disease and therefore, early detection of BM micrometastasis may identify high-risk patients for additional systemic therapy. More so, BM provides a readily accessible source to serially monitor subclinical disease progression and the potential impact of adjuvant therapies early in the disease course. Conventional histologic analysis of BM aspirates for tumor cells has proven unreliable[3,4]. More recently, immunocytochemical techniques using antibodies to epithelial antigens expressed on tumor cells have improved detection sensitivity. However, assay reliability has been shown to be highly dependent on the antibody selected as well as the variability by which the tumor cell expresses the preferred epitope[8,11]. Finally, sample processing and antibody staining require considerable attention to methodology and an experienced reviewer to interpret the results.

With the implication of an accrual of aberrant genetic events in tumor development and progression, and their potential for clonality, these genetic markers may provide unique surrogates for monitoring subclinical disease events, particularly in light of the ease and widespread use of PCR techniques. Studies have demonstrated the presence of circulating nucleic acids in the plasma and serum of patients with various malignancies[32]. In breast cancer, LOH presence in plasma/serum has been described to occur anywhere from 15% to 66%[19,21-23,30]. These results may vary due to differences in the techniques of sample collection and processing, DNA isolation, PCR methods, and scoring of LOH. Furthermore, in the earlier work, the inventors have shown that the presence of the circulating tumor DNA increases with the advancing stage of disease[23]. Since BM is a frequent site of melanoma, prostate, colorectal and breast cancer relapse, it was an object of the present invention to determine whether BM aspirates harbor tumor-specific DNA alterations associated with early breast cancer progression.

The present invention provides highly sensitive methods of detecting tumor-specific DNA in the BM aspirates, plasma/serum, and tumor tissue of cancer patients, including melanoma, breast, colorectal, and prostate cancer patients. The increased incidence in the more advanced stages correlates with tumor burden and therefore may have applicability as a surrogate marker for disease detection, prognosis, and monitoring tumor progression and response to therapy. The present invention demonstrates an association between known prognostic factors in breast cancer (tumor histopathology, tumor size, lymph node status, and AJCC stage) and an incidence of LOH and methylation markers in BM, blood (plasma/serum), and primary tumor and metastatic tissues.

Some advantages of the methods of the present invention over conventional methods include the ease of their use, high sensitivity and specificity, and their broad application to a variety of malignancies. Additional tumor-specific genetic markers or combinations thereof may be easily incorporated into methods of the present invention to further enhance the assay's utility.

The methods of the present invention may provide a unique alternative/supplement to optical systems for occult tumor detection which can be technically demanding and viewer dependent. The methods of the present invention may also provide an alternative/supplement to RT-PCR methods that assess mRNA markers which may have limited specificity as a result of unstable gene products, variable expression levels, and nonspecific transcripts[39-42]. The inventors believe that the detection of genomic alterations in BM may offer more specificity than immunohistochemical and/or current mRNA marker assays.

In one study, which is described in more detail in Example 5, the inventors observed LOH in BM ranging from 0% to 12% for various microsatellite markers (see Table 10). A similar detection of LOH has been described from the peripheral plasma/serum of early stage breast cancer patients[19,22,23]. For 10 of the 11 patients whose BM contained LOH, primary tumor blocks were available for assessment and in all cases, a similar corresponding LOH pattern was identified in the respective primary tumor specimens. The findings demonstrate the specificity of this marker detection system.

In the study discussed in Example 5, no patients had detectable tumors cells identified on routine histopathologic examination. This demonstrates the relative ease and sensitivity that the methods of the present invention provide in the identification and diagnosis of subclinical disease. Because of the earlier detection of breast cancers and the benefits of adjuvant radiotherapy, immunotherapy, and chemotherapy in these stages, the methods and microsatellite markers of the present invention provide improved occult disease surveillance and ability to assess individual patient risk more accurately. This allows modification of treatment strategies before clinical manifestations occur.

Breast cancer recurrence is a result of undetected metastasis at the time of primary patient treatment. More sensitive methods are needed to identify subclinical disease progression to better accompany those increasing advances in early breast cancer screening. Aberrant hypermethylation of tumor-suppressor genes is found frequently in primary breast tumors and has been implicated in disease initiation and progression. The increased sensitivity for the detection of methylated genes associated with a cancer phenotype among a background of unmethylated genes from normal cells offers a potential specific surrogate marker for molecular detection of occult disease progression. We evaluated whether tumor-associated methylated DNA markers could be identified circulating in BM aspirates and paired serum samples from 33 early-stage patients undergoing surgery for breast cancer. Methylation specific PCR was performed using a tumor-related gene panel for RAR-β2, MGMT, RASSF1A and APC. Tumor-associated hypermethylated DNA was identified in 7 (21%) of 33 BM aspirates and 9 (27%) serum samples. In three patients, the bone marrow and serum were positive for hypermethylation. The most frequently detected hypermethylation marker was RASSF1A occurring in 7 (21%) patients. Concordance was present between gene hypermethylation detected in BM/serum samples and matched-pair primary tumors. Advanced AJCC stage was associated with an increased incidence of circulating gene hypermethylation. This study demonstrates the novel finding of tumor-associated epigenetic markers in BM aspirates and their potential role as targets for molecular detection and as an aid to early-stage breast cancer patient risk identification.

Gene promoter region hypermethylation is a frequent event in primary breast cancer. However its impact on tumor progression and potential prognostic implications remain relatively unknown. We conducted hypermethylation profiling of 151 primary breast tumors with association to known prognostic factors in breast cancer using methylation specific PCR for six known tumor suppressor and related genes: RASSF1A, APC, Twist, CDH1, GSTP1 and RAR-β2. Furthermore correlation with sentinel lymph node tumor status was assessed as it represents the earliest stage of metastasis that can be readily detected. Hypermethylation for any one gene was identified in 147 (97%) of 151 primary breast tumors. The most frequently hypermethylated gene was RASSF1A (81%). Hypermethylation of the CDH1 was significantly associated with primary breast tumors demonstrating lymphovascular invasion (p=0.008), infiltrating ductal histology (p=0.03), and negative for the estrogen receptor (p=0.005), whereas RASSF1A and RAR-β2 gene hypermethylation were significantly more common in ER positive (p<0.001) and HER2 positive (p<0.001) tumors, respectively. In multivariate analysis, hypermethylation of GSTP1 and/or RAR-β2 was significantly associated with patients have macroscopic sentinel lymph node metastasis, odds ratio 4.59 (95% CI, 2.02 to 10.4; p<0.001). Hypermethylation profiling of primary breast cancers may have clinical and pathologic utility for assessing patient prognosis and predicting early lymph node regional metastasis.

Aberrant methylation of CpG islands in promoter regions of tumor suppressor genes (TSG) has been demonstrated in epithelial origin tumors. However, the methylation profiling of tumor-related gene promoter regions in cutaneous melanoma tumors has not been reported. Seven known or candidate TSGs that are frequently hypermethylated in carcinomas were assessed by methylation-specific polymerase chain reaction (MSP) in 15 melanoma cell lines and 130 cutaneous melanoma tumors. Four TSGs were frequently hypermethylated in 86 metastatic tumor specimens: retinoic acid receptor-β2 (RAR-β2) (70%), RAS association domain family protein 1A (RASSF1A) (57%), and $O^6$-methylguanine DNA methylatransferase (MGMT) (34%), and death-associated protein kinase (DAPK) (19%). Hypermethylation of MGMT, RASSF1A, and DAPK was significantly lower in primary melanomas (n=20) compared to metastatic melanomas. However, hypermethylation of RAR-β2 was 70% in both primary and metastatic melanomas. Cell lines had hypermethylation profiles similar to those of metastatic melanomas. The analysis of these four markers of metastatic tumors demonstrated that 97% had ≧1 gene(s) and 59% had ≧2 genes hypermethylated, respectively. The methylation of genes was verified by bisulfite sequencing. The mRNA transcripts could be re-expressed in melanoma cell lines having hypermethylated genes following treatment with 5'-aza 2'-deoxycytidine (5Aza-dC). Analysis of melanoma patients' plasma (preoperative blood; n=31) demonstrated circulating hypermethylated MGMT, RAR-β2, and RASSF1A DNA for at least one of the markers in 29% of the patients. Our findings indicate that the incidence of TSG hypermethylation increases during tumor progression. Methylation of TSG may play a significant role in cutaneous melanoma progression.

Cancer cells almost invariably undergo loss of genetic material (DNA) when compared to normal cells. This deletion of genetic material which almost all, if not all, varieties of cancer undergo is referred to as "loss of heterozygosity" (LOH). The loss of genetic material from cancer cells can result in the selective loss of one of two or more alleles of a gene vital for cell viability or cell growth at a particular locus on the chromosome. All genes, except those of the two sex chromosomes, exist in duplicate in human cells, with one copy of each gene (allele) found at the same place (locus) on each of the paired chromosomes. Each chromosome pair thus contains two alleles for any gene, one from each parent. This redundancy of allelic gene pairs on duplicate chromosomes provides a safety system. If a single allele of any pair is defective or absent, the surviving allele will continue to produce the coded protein.

Due to the genetic heterogeneity or DNA polymorphism, many of the paired alleles of genes differ from one another. When the two alleles are identical, the individual is said to be homozygous for that pair of alleles at that particular locus. Alternatively, when the two alleles are different, the individual is heterozygous at that locus. Typically, both alleles are transcribed and ultimately translated into either identical proteins in the homozygous case or different proteins in the heterozygous case. If one of a pair of heterozygous alleles is lost due to deletion of DNA from one of the paired chromosomes, only the remaining allele will be expressed and the affected cells will be functionally homozygous. This situation is termed as "loss of heterozygosity" (LOH) or reduction to homozygosity. Following this loss of an allele from a heterozygous cell, the protein or gene product thereafter expressed will be homogeneous because all of the protein will be encoded by the single remaining allele. The cell becomes effectively homozygous at the gene locus where the deletion occurred. Almost all, if not all, cancer cells undergo LOH at some chromosomal regions.

Through the use of DNA probes, DNA from an individual's normal cells can be compared with DNA extracted from the same individual's tumor cells and LOH can be identified using experimental techniques well known in the art. Alternatively, LOH can be assayed by demonstrating two polymorphic forms of a protein in normal heterozygous cells, and only one form in cancer cells where the deletion of an allele has occurred. See, for example, Lasko et al, 1991, Annu. Rev. Genet. 25:281-314.

Recent advances in molecular biology have revealed that genesis and progression of tumors follow an accumulation of multiple genetic alterations, including inactivation of tumor suppressor genes and/or activation of proto-oncogenes. There are over 40 known proto-oncogenes and suppressor genes to date, which fall into various categories depending on their functional characteristics. These include, growth factors and growth factor receptors, messengers of intracellular signal transduction pathways, for example, between the cytoplasm and the nucleus, and regulatory proteins influencing gene expression and DNA replication. Frequent LOH on specific chromosomal regions has been reported in many kinds of malignancies, which indicates the existence of putative tumor suppresser genes or tumor-related genes on or near these loci. LOH analysis is a powerful tool to search for a tumor suppresser gene by narrowing and identifying the region where a putative gene exists. By now, numerous LOH analyses, combined with genetic linkage analysis on pedigrees of familial cancer (Vogelstein et al, 1988, New England Journal of Medicine 319(9):525-532; Fearon et al., 1990, Cell 61:759-767; and Friend et al., 1986, Nature 323:643-646) or homozygous deletion analyses (Call et al., 1990, Cell 60:509-520; Kinzler et al., 1991, Science 253:661-665; and Baker et al., 1989, Science 244:217-221) have identified many kinds of candidate tumor suppressor or tumor-related genes. Also, because allelic losses on specific chromosomal regions are the most common genetic alterations observed in a variety of malignancies, microsatellite analysis has been applied to detect DNA of cancer cells in specimens from body fluids, such as sputum for lung cancer and urine for bladder cancer (Rouleau et al., 1993, Nature 363:515-521; and Latif et al., 1993, Science 260:1317-1320). Moreover, it has been established that markedly increased concentrations of soluble DNA are present in plasma of individuals with cancer and some other diseases, indicating that cell free serum or plasma can be used for detecting cancer DNA with microsatellite abnormalities (Kamp et al., 1994, Science 264:436-440; and Steck et al., 1997, Nature Genetics 15:356-362). Two groups have reported microsatellite alterations in plasma or serum of a limited number of patients with small cell lung cancer or head and neck cancer (Hahn et al., 1996, Science 271:350-353; and Miozzo et al., 1996, Cancer Research 56:2285-2288).

Recent developments in cancer therapeutics have demonstrated the need for more sensitive staging and monitoring procedures to ensure initiation of appropriate treatment, to define the end points of therapy and to develop and evaluate novel treatment modalities and strategies. In the management of cancer patients, the choice of appropriate initial treatment depends on accurate assessment of the stage of the disease. Patients with limited or regional disease generally have a better prognosis and are treated differently than patients who have distant metastases (Minna et al., 1989, Cancer Principals and Practices of Oncology, DeVita et al., ed., Lippincott, Philadelphia 591-705). However, conventional techniques to detect these metastases are not very sensitive, and these patients are often not cured by primary tumor resection because they have metastases that are not identified by standard methods during preoperative staging. Thus, more sensitive methods to detect metastases in other types of carcinomas would identify patients who will not be cured by local therapeutic measures, for whom effective systemic therapies would be more appropriate.

The strategy of the present invention is to utilize genetic differences between normal and cancer cells for diagnosis and monitoring of cancer patients. Many genes coding for proteins or other factors vital to cell survival and growth that are lost, can be identified through LOH analysis of microsatellite, single nucleotide polymorphism (SNP) loci in cancer cells and mapped to specific chromosomal regions. Gene expression may be suppressed due to hypermethylation in the promoter region or mutation in the gene. In melanoma, mutations of several already-known tumor suppresser genes such as p53 gene, neurofibromatosis 1 (NF1) gene, and NF2 gene have been reported at a low frequency and deletions and/or mutations of the cyclin dependent kinase 4 (CDK4) inhibitor gene, which is a responsible tumor suppresser gene for a familial melanoma, have been thought to be important genetic changes in tumor development (Miozzo et al., 1996, Cancer Research 56:2285-2288). In addition to the locus of CDK4 inhibitor gene (9p21), frequent chromosomal deletions have been reported on 1p36, 3p25, 6q22-q26, 10q24-q26, and 11q23. (Mao et al, 1996, Science 271:659-662; Stroun et al., 1987, Eur. J. Cancer Clin. Oncol. 23(6):707-712; Chen et al., 1996, Nature Medicine 2(9):1033-1035; and Nawroz et al., 1996, Nature Medicine 2(9):1035-1037). An efficient method of testing DNA microsatellite or SNP loci for LOH, hypermethylation in the promoter region of a gene, and mutations in a gene allows early diagnosis of melanoma patients and monitoring of the progression of the disease as well as effectiveness of the therapeutic regimen.

A cellular DNA can be obtained from a sample of a biological fluid by deproteinizing the sample and extracting DNA according to the procedures well known in the art. Examples of biological fluids include urine, blood plasma or serum, sputum, cerebral spinal fluid, peritoneal fluid, ascites fluid, saliva, stools, and bone marrow plasma. The DNA to be tested may be a fraction of a larger molecule or can be present initially as a discrete molecule. Where the test DNA contains two strands, it may be necessary to separate the strands of the nucleic acid before it can be used, e.g., as a template for amplification. Strand separation can be effected either as a separate step or simultaneously with synthesis of primer extension products. This strand separation can be accomplished using various suitable denaturing conditions, including physical, chemical, or enzymatic means. If the nucleic acid is single stranded, its complement is synthesized by adding one or two oligonucleotide primers. If a single primer is utilized, a primer extension product is synthesized in the presence of primer, an agent for polymerization, and the four nucleoside triphosphates. The product will be complementary to the single-stranded nucleic acid and will hybridize with a single-stranded nucleic acid to form a duplex of unequal length strands that may then be separated into single strands to produce two single separated complementary strands.

A DNA marker refers to a DNA sequence (e.g., a microsatellite or SNP locus, a promoter region, or a gene sequence) associated with a specific biological event (e.g., presence or absence of a gene, hypermethylation of a promoter, mutation in a gene, expression of a gene, and occurrence of a disease). Microsatellites are short repetitive sequences of DNA widely distributed in the human genome. Somatic alterations in the repeat length of such microsatellites have been shown to represent a characteristic feature of tumors. SNP is a common nucleotide variant in DNA at a single site. Each individual has many single nucleotide polymorphisms that together create a unique DNA sequence. These markers can be tested either independently or in combination with each other.

Detection of a DNA marker can be accomplished by a number of means well known in the art. One means of detecting a DNA marker is by digesting a test DNA sample with a restriction endonuclease. Restriction endonucleases are well known in the art for their ability to cleave DNA at specific sequences, and thus generate a discrete set of DNA fragments from each DNA sample. The restriction fragments of each DNA sample can be separated by any means known in the art. For example, agarose or polyacrylamide gel electrophoresis can be used to electrophoretically separate fragments according to physical properties such as size. The restriction fragments can be hybridized to nucleic acid probes which detect restriction fragment length polymorphisms (RFLP). There are various hybridization techniques known in the art, including both liquid and solid phase techniques. One particularly useful method employs transferring the separated fragments from an electrophoretic gel matrix to a solid support such as nylon or filter paper so that the fragments retain the relative orientation which they had on the electrophoretic gel matrix. The hybrid duplexes can be detected by any means known in the art, for example, by autoradiography if the nucleic acid probes have been radioactively labeled. Other labeling and detection means are well known in the art and may be used accordingly.

An alternative means for detecting a DNA marker is by using PCR (polymerase chain reaction; see, e.g., U.S. Pat. Nos. 4,683,195, 4,683,202, and 4,683,194). This method allows amplification of discrete regions of DNA containing microsatellite sequences. Amplification is accomplished by annealing, i.e., hybridizing a pair of single stranded primers, usually comprising DNA, to a target DNA. The primers embrace oligonucleotides of sufficient length and appropriate sequence so as to provide specific initiation of polymerization of a significant number of nucleic acid molecules containing the target nucleic acid. In this manner, it is possible to selectively amplify the specific target nucleic acid sequence containing the nucleic acid of interest. More specifically, the primers are designed to be substantially complementary to each strand of target nucleotide sequence to be amplified. Substantially complementary means that the primers must be sufficiently complementary to hybridize with their respective strands (i.e., with the flanking sequences) under conditions which allow amplification of the nucleotide sequence to occur. The primer is preferably single stranded for maximum efficiency in amplification but may be double-stranded. If double-stranded, the primer is first treated to separate its strands before being used to prepare extension products. Preferably, the primer is an oligodeoxyribonucleotide. The primer must be sufficiently long to prime the synthesis of extension products in the presence of the inducing agent for polymerization. The exact length of a primer will depend on many factors, including temperature, buffer, and nucleotide composition. The oligonucleotide primers for use in the present invention may be prepared using any suitable method, such as conventional phosphotriester and phosphodiester methods or automated embodiments thereof. In one such automated embodiment, diethylphosphoramidites are used as starting materials and may be synthesized as described by Beaucage et al. (Tetrahedron Letters 22:1859-1862, 1981). One method for synthesizing oligonucleotides on a modified solid support is described in U.S. Pat. No. 4,458,066. The primers are annealed to opposite strands of the DNA sequence containing a DNA marker, such that they prime DNA synthesis in opposite but convergent directions on a chromosome. Amplification of the region containing the DNA marker is accomplished by repeated cycles of DNA synthesis. Experimental conditions conducive to synthesis include the presence of nucleoside triphosphates and an agent for polymerization, such as DNA polymerase, and a suitable temperature and pH. Preferably, the DNA polymerase is Taq polymerase which is relatively heat insensitive. The amplification procedure includes a specified number of cycles of amplification in a DNA thermal cycler. After an initial denaturation period of 5 minutes, each amplification cycle preferably includes a denaturation period of about 1 minute at 95° C., primer annealing for about 2 minutes at 58° C., and an extension at 72° C. for approximately 1 minute. Following the amplification, aliquots of amplified DNA from the PCR can be analyzed by techniques such as electrophoresis through agarose gel using ethidium bromide staining. Improved sensitivity may be attained by using labeled primers and subsequently identifying the amplified product by detecting radioactivity or chemiluminescense on film.

In a preferred embodiment, the assay involves labeling of the PCR primers with multiple types of chromophore dyes. In another embodiment, the PCR primers are labeled with an atom or inorganic radical, most commonly using radionuclides, but also perhaps heavy metals. Radioactive labels include $^{32}P$, $^{125}I$, $^{3}H$, $^{14}C$, or any radioactive label which provides for an adequate signal and has sufficient half-life. Other labels include ligands, which can serve as a specific binding pair member for a labeled ligand, and the like.

Another object of the invention is to provide a method of detecting DNA markers in biological fluids, wherein the presence of LOH, hypermethylation, or mutation is associated with the occurrence of cancer. This method represents a significant advance over such techniques as tissue biopsy by providing a non-invasive, rapid, and accurate method for detecting DNA markers associated with cancer. Thus, the present invention provides a method which can be used to screen high-risk populations and to monitor high risk patients undergoing chemoprevention, chemotherapy, immunotherapy, surgical procedure, or other treatment.

According to the method of the present invention, DNA is isolated from a biological fluid of a patient. For comparison, a control DNA sample may be prepared, for example, from a non-neoplastic tissue from the same patient, or from a biological fluid or tissue from a normal person. It is desirable that the alleles used in the allelotype loss analysis be those for which the subject is heterozygous. Determination of heterozygosity is well within the skill of the art. Loss of an allele is ultimately determined by comparing the pattern of bands corresponding to the allele in the control sample to the test sample and noting the size, number of bands, or level of amplification of signal of individual bands. For example, LOH may be defined when one allele showed more than a threshold degree (e.g., $\geq 50\%$) reduction of peak intensity for serum DNA as compared to the corresponding allele identified in the control DNA. Methods of detecting hypermethylation of DNA (see Examples below) and mutations in a gene are well known in the art.

This invention also provides a logistically practical assay to monitor the genetic changes during cancer progression. The events of tumor progression are dynamic and the genetic changes that concurrently occur also are very dynamic and complex. The most significant advantage of this approach compared to other approaches is the ability to monitor disease progression and genetic changes without assessing the tumor. This is particularly important during early phases of distant disease spread, in which subclinical disease is undetectable by conventional imaging techniques. In addition, in advance stage diseases or inoperable sites in which tumor tissue is very difficult or impossible to obtain for genetic analysis, the present invention provides an alternative for assessing LOH, DNA hypermethylation, and gene mutation.

Because the methods described above require only DNA extraction from bodily fluid such as blood, it can be performed at any time and repeatedly on a single patient. Blood can be taken and monitored for LOH, DNA hypermethylation, and gene mutation before or after surgery; before, during, and after treatment, such as chemotherapy, radiation therapy, gene therapy or immunotherapy; or during follow-up examination after treatment for disease progression, stability, or recurrence. The method of the present invention also may be used to detect subclinical disease presence or recurrence with a DNA marker specific for that patient since DNA markers are specific to an individual patient's tumor. The method also can detect if multiple metastases may be present using tumor specific DNA markers.

Further, the invention provides predictive measures of response to cancer therapies and mortality. The method comprises providing a sample from the subject and detecting one or more DNA markers in the sample, wherein the status of the DNA markers are indicative of response to cancer therapies and mortality. More specifically, the invention provides a method of predicting the probability of survival of a subject suffering from a cancer. For example, if LOH, DNA hypermethylation and/or gene mutation occur in a cancer patient, the patient is expected to have a low probability of survival.

LOH, DNA hypermethylation and gene mutation can also be detected in a tissue sample (e.g., a tumor sample). For a tumor sample, if a non-neoplastic tissue is used as a control sample, it can be of the same type as the neoplastic tissue or from a different organ source. It is desirable that the neoplastic tissue contains primarily neoplastic cells and that normal cells be separated from the neoplastic tissue. Ways for separating cancerous from non-cancerous cells are known in the art and include, for example, microdissection of tumor cells from normal cells of tissues, DNA isolation from paraffin-embedded sections and cryostat sections, as well as flow cytometry to separate aneuploid cells from diploid cells. DNA can also be isolated from tissues preserved in paraffin. Separations based on cell size or density may also be used. Once the tissues have been microdissected, DNA can be isolated from the tissue using any means known in the art. Frozen tissues can be minced or homogenized and then the resulting cells can be lysed using a mixture of enzyme and detergent, see, for example, Maniatis, Molecular Cloning, a Laboratory Manual, Cold Spring Harbor Laboratory, 1982. The nucleic acids can be extracted using standard techniques such as phenol and chloroform extraction, and ethanol precipitation.

It is another object of the invention to provide kits and packaged products for diagnosing, staging and monitoring cancer patients. Such a kit or product usually contains a set of reagents for detecting LOH, DNA hypermethylation, and gene mutation. For example, a kit or product may include nucleic acid probes for specified alleles for which the patient is homozygous or heterozygous to detect LOH in these specified alleles. This provides a measure of the extent of genetic change in a neoplastic tissue or a biological fluid which can be correlated with a diagnosis or prognosis. In one specific embodiment, the presence or absence of a specific allele or combination of alleles is tested by amplification of regions of the DNA markers using pairs of primers which bracket specific regions of the DNA markers on specific chromosome arms containing repeat sequences with polymorphism. Preferably, the assay uses fluorescent labeling of DNA with multiple types of chromophores. However, radioactive and other labeling techniques known in the art also may be used. Optionally, the kit or product may include a container, and an insert associated with the container. The insert may be a label or an instruction sheet with the information as to, e.g., what sample to use and what the indication is if LOH, DNA hypermethylation or gene mutation is detected.

The kit or product may comprise a carrier means being compartmentalized to receive in close confinement one or more container means such as vials, tubes, and the like, each of the container means comprising one of the separate elements to be used for detecting DNA markers. Such elements include a labeled primer pair for amplifying a DNA marker. The product also may include a DNA polymerase for amplifying the target DNA, appropriate amplification buffers and deoxyribonucleoside triphosphates. The nucleic acids in the product may be provided in solution or lyophilized form. Preferably, the nucleic acids will be sterile and devoid of nucleases to maximize shelf-life.

The following examples are intended to illustrate, but not to limit, the scope of the invention. While such examples are typical of those that might be used, other procedures known to those skilled in the art may alternatively be utilized. Indeed, those of ordinary skill in the art can readily envision and produce further embodiments, based on the teachings herein, without undue experimentation.

EXAMPLES

Example 1

Identification of Circulating Tumor-Associated Epigenetic Alterations in the Bone Marrow from Breast Cancer Patients Using a Hypermethylation Gene Panel Introduction A variety of genetic alterations including microsatellite instability, allelic loss, and mutation have been described in primary breast cancers. These events result in loss of gene function and have been implicated in tumor development and progression. Clinical tools (i.e., radiographic) used to detect breast cancer progression have been limited particularly in the era of earlier disease diagnosis. The most sensitive method for the identification of breast cancer progression at the time of patient diagnosis is histopathologic lymph node evaluation. However 20-30% of node-negative breast cancer patients will develop recurrent disease within 10 years [Fisher, 1989 #178][Rosen, 1989 #30]. Therefore, recurrence may be considered a consequence of occult metastasis not detected at the time of patient diagnosis and treatment. The most frequent site of breast cancer metastasis is bone [Goldhirsch, 1988 #179]. Identification of patients at increased risk for systemic metastasis may improve prognostic staging and provide selection for additional therapy that may have a significant impact on disease outcome. Assessment of body fluids for circulating tumor cells using microscopy has shown poor results [Molino, 1991 #180]. This technique is labor-intensive, insensitive and subjective. Furthermore, the rapid circulation and turbulent environment of blood may contribute to the low yield. In contrast, detection of occult tumor cells in BM using immunocytokeratins has been associated with the subsequent development of systemic metastasis and shows promise marker of a poorer prognostic outcome [Braun, 2000 #4]. Regardless, identification of a few tumor cells among a background of one million normal BM cells can be difficult and tedious. Automated techniques such as RT-PCR can facilitate identification with improved sensitivity but may have diminished specificity as tumor cell specific mRNA markers are uncommon and expression levels may vary substantially affecting results.

Recently cell-free DNA has been identified in the serum and plasma from patients with various cancers [Sidransky, 1997 #171]. These circulating nucleic acids have demonstrated similar genetic alterations and characteristics as those found in the primary tumor. Their presence in blood can be readily identified using common PCR techniques and appear to be elevated during disease progression [Silva, 1999 #85][Taback, 2001 #181][Muller, 2003 #77][Silva, 2002 #83].

Alternatively, promoter region hypermethylation has been described as a common genetic abnormality occurring in various cancers. Aberrant methylation of CpG islands in promoter regions of putative tumor-suppressor and related genes resulting in their silencing has been implicated in oncogenesis. Identification of these additional genetic events may offer a more accurate molecular portrait accounting for a tumor's metastatic potential and provide unique tumor-specific surrogate markers for monitoring occult disease progression. Methylation-specific real-time PCR provides a highly sensitive DNA based assay for the detection of methylated alleles associated with breast cancer [Esteller, 2001 #65].

Because BM is the most common site for systemic relapse following breast cancer diagnosis, we attempted to determine whether BM aspirate plasma could provide a viable source to detect tumor-specific epigenetic alterations associated with systemic metastasis from early stage breast cancer patients.

Methods and Materials

Surgical Specimens and DNA Isolation. BM aspirates were collected prospectively in 4.5 ml sodium citrate tubes (Becton Dickinson, Franklin Lakes, N.J.) through bilateral anterior iliac approach from 33 consecutive patients as follows: 17 American Joint Committee on Cancer (AJCC) stage I patients, 14 AJCC stage II patients, and 2 AJCC stage III patients; undergoing surgical resection of their primary breast cancer at the Saint John's Health Center/John Wayne Cancer Institute. In addition, BM aspirates were obtained from five healthy female volunteer donors to serve as controls. Institutional Review Board approved consent forms were signed by all patients prior to participation in the study. BM was drawn and (cell-free supernatant) plasma was separated, filtered and cryopreserved as previously described [Taback, 2003 #163]. In addition, match-paired peripheral venous blood was drawn pre-operatively and DNA was extracted from one ml of both peripheral blood serum and BM aspirate plasma using QIAamp extraction kit (Qiagen, Valencia, Calif.) as previously described (23).

To determine the correlation of gene hypermethylation found in the primary breast tumor, DNA was isolated from ten 10 μm sections cut from paraffin-embedded tissue blocks. Samples were deparaffinized, microdissected from normal tissue using laser capture microscopy (Arcturus, Mountain View, Calif.) and incubated in lysis buffer and proteinase K at 37° C. overnight as described previously.

Gene hypermethylation in BM of tumor DNA was analyzed as described below. Additionally, each BM aspirate was assessed for the presence of occult tumor cells by standard histologic staining methods using hematoxylin and eosin (H&E).

Gene Hypermethylation Markers and MSP. Sodium bisulfite modification was performed on 1 ug of genomic DNA as previously described [Hoon, 2004 #176]. Primer sets were used for the detection of four genes frequently hypermethylated in breast cancer: RAS association domain family protein 1 A protein (RASSF1A), adenomatous polyposis coli (APC), retinoic acid binding receptor-β2 (RAR-β2) and MGMT. In addition, MYOD was assessed as an internal control to confirm DNA presence in the final reaction. MSP was performed with an initial incubation for 15 min at 95° C. followed by 35 cycles (40 cycles for BM and plasma aspirate samples) of denaturation at 94° C. for 30 s, annealing at 50-56° C., and extension for 90 s at 72° C., followed by a final extension step of 72° C. for 5 min. For each MSP reaction, normal donor lymphocyte DNA served as a negative control, SssI treated lymphocyte served as a positive control, and water served as a control for contamination.

Clinical and pathologic data was obtained from John Wayne Cancer Institute's Breast Tumor Computer Database. Chi-Square and Wilcoxon Rank Sum tests were performed for statistical evaluation for the association of BM methylation status and known prognostic parameters in breast cancer.

Results

Circulating tumor DNA containing gene promoter hypermethylation for any one marker was identified in the BM of 7 (21%) of 33 patients. The most frequently detected hypermethylated gene marker was RASSF1A occurring in 5 (15%) patients BM, followed by MGMT in 2 (6%) patients, RAR-β2 and APC in 1 (3%) patient each Table 1. Five patients demonstrated one hypermethylated gene in their BM, whereas two patients had two hypermethylated genes identified and in twenty-six patients no hypermethylated DNA sequences could be detected for any of the genes assessed. No hypermethylation was detected in the BM from five healthy female donors.

TABLE 1

Frequency of gene hypermethylation in patient's serum and bone marrow

| | Frequency in Patients' Body Fluid (n = 33) | |
|---|---|---|
| Marker | Serum | Bone Marrow |
| RASSF1A | 5 (15%) | 7 (21%) |
| MGMT | 2 (6%) | 2 (6%) |
| RARβ | 1 (3%) | 2 (6%) |
| APC | 1 (3%) | 0 |

There was an increased association between the presence of gene hypermethylation detected in the BM and advanced disease stage. Three (18%) of 17 AJCC stage I patients demonstrated hypermethylated DNA for at least one marker in their BM, in contrast to 3 (21%) of 14 AJCC stage II patients, and 1 (50%) of 2 AJCC stage III patients (Table 2).

TABLE 2

Gene hypermethylation detection in breast cancer patient's serum and bone marrow according to AJCC stage

| | Patients with hypermethylation | |
|---|---|---|
| AJCC Stage | Serum | Bone Marrow |
| I (n = 17) | 4 (24%) | 3 (18%) |
| II (n = 14) | 4 (29%) | 3 (21%) |
| III (n = 2) | 1 (50%) | 1 (50%) |

Hypermethylation was detected in paired peripheral blood serum in 9 (27%) of 33 patients. Again RASSF1A was most frequently identified occurring in 7 (21%) patients serum samples followed by RAR-β2 (6%) and MGMT (6%) (Table 1). Eight patients demonstrated hypermethylation in serum for one gene and one patient for 3 genes. Similarly, there was an increased association between the presence of gene hypermethylation in serum and advanced AJCC stage. Hypermethylation for any one gene was identified in 4 (24%) of 17 AJCC stage I patients serum, whereas 4 (29%) of 14 AJCC stage II patients, and 1 (50%) of 2 AJCC stage III patients had these findings (Table 2).

Twelve clinicopathologic prognostic factors were assessed for correlation with BM methylation status: patient age, histologic tumor type, size, grade, Bloom-Richardson score, lymph node involvement, AJCC stage, receptor status (estrogen (ER), progesterone (PR), HER2), Ki-67 and p53 status. A trend towards increased circulating methylated DNA in serum from patients with PR negative tumors was identified: 5 (50%) of 10 patients as compared to 4 (18%) of 23 patients with PR positive tumors. In multivariate analysis, patients with PR positive tumors were less likely to have methylation markers in their BM and serum, odds ratio 0.04, 95% CI: 0.00-0.82 (p<0.04). However, due to the small sample size, no other correlations were identified with BM or serum methylation status.

Concordance between the presence of serum and/or BM hypermethylation status among patients is shown in Table 3. However, identification of the same gene hypermethylated between the BM and serum occurred in only 2 patients, with one additional patient having the same gene hypermethylation profile in BM for two of the three genes detected in serum.

TABLE 3

Hypermethylation status: concordance between patient's serum and bone marrow

|  |  | Serum | |
| --- | --- | --- | --- |
|  |  | Yes | No |
| Bone Marrow | Yes | 3 | 4 |
|  | No | 6 | 20 |

Yes: presence of hypermethylation detected for any one gene
No: absence of hypermethylation detected for any genes To determine whether a correlation existed between the gene hypermethylation detected in patients BM and their primary tumor, DNA was isolated from primary tumors and evaluated with the same hypermethylation markers. Of 13 patients with BM and/or serum positive for gene hypermethylation, 8 had primary tumor blocks available for assessment. In all eight patients, the hypermethylated gene(s) identified in the BM/serum was also hypermethylated respectively in the primary tumor.

Conventional histologic analysis of all specimens using standard H&E staining did not demonstrate occult tumor cells in any of the BM samples.

Discussion

Advances in breast imaging modalities and greater awareness for early detection has resulted in a dramatic increase in the number of smaller breast cancer diagnosed. Concurrently, these tumors are less likely to be associated with readily identified metastasis. However, patients with small primary tumors are not exempt from developing recurrent disease, and these relapses are most likely a consequence of occult metastasis present at the time of initial diagnosis and treatment. Thus, improved methods are needed to detect submicroscopic disease which can identify patients at increased risk for recurrence sooner in their treatment course. Additionally, techniques that detect occult metastasis may better stratify those patients with subclinical disease that may benefit from adjuvant therapy while more accurately recognizing patients who do not require additional treatment.

MSP provides a highly sensitive and quantitative technique that can identify 1 methylated allele among a background of 1000 normal alleles [Herman, 1996 #177], and therefore may prove useful for assessing the presence of occult disease and increased patient risk. Additionally, this approach allows for the identification of novel aberrantly hypermethylated genes, which may be associated with breast cancer tumor growth and metastasis and thereby distinguish additional potential targets for therapy. In this study, we identified tumor-associated epigenetic alterations circulating in the blood and BM from 4 (18%) of 22 early stage breast cancer patients without evidence of lymph node metastasis. It is estimated that 20-30% of node-negative patients will develop a systemic recurrence by 10 years and younger patients remain at risk for relapse many decades after diagnosis [Brenner, 2004 #182]. Thus longer-term follow-up to determine whether these findings are associated with disease recurrence in this group of patients will be needed. However, these findings provide a promising potential for analyzing circulating nucleic acids in body fluids from patients with breast cancer for assessing the earliest stages of disease progression. Recently, investigators have shown DNA methylation in breast cancer patients serum to correlate with a worse survival [Muller, 2003 #77]. We have previously demonstrated the presence of LOH in the BM from patients with breast cancer [Taback, 2003 #163]. These findings are significant because bone is the most frequent site of systemic metastasis. Therefore, performing a comprehensive assessment of a patients body fluids, particularly the location most common for relapse, may yield highly informative information, improve risk assessment and allow for a more accurate method for monitoring treatment responses earlier in the disease course. Innovative techniques are needed to detect and characterize subclinical disease progression in this new era of early breast cancer diagnosis.

Example 2

Distinct Hypermethylation Profile of Primary Breast Cancer is Associated with Sentinel Lymph Node Metastasis Introduction Improved access to mammography and increased patient awareness in breast cancer screening have resulted in a dramatic increase in the detection of early breast cancers [Cady, 1996 #2; Shapiro, 1982 #4; Tabar, 1985 #7; Miller, 1993 #9]. As important, at the time of breast cancer diagnosis, is the identification of concurrent metastatic disease for accurate patient staging and therapeutic decision making. Axillary lymph node dissection (ALND) has provided an invaluable approach to assess for the presence of tumor cell metastasis, particularly in early disease states where standard radiographic imaging is less sensitive. However, ALND can be associated with considerable morbidity including lymphedema and reduced shoulder mobility [Ivens, 1992 #39; Warmuth, 1998 #80]. In addition, ALND often requires general anesthesia, in patient hospitalization and a postoperative drain. Evidence from prospective randomized trials has questioned the therapeutic value of routine ALND in patients without palpable disease [, 1980 #44; Fisher, 1985 #43; Cabanes, 1992 #136].

Sentinel lymph node (SLN) biopsy provides an effective alternative approach to the identification of regional nodal metastasis, and is associated with reduced morbidity when compared to standard ALND [Giuliano, 2000 #21]. This procedure, although less invasive, is not entirely risk-free as it still requires an axillary incision and general anesthesia, subjects patients to lymphatic mapping reagents and its success is dependent on the skill of the surgeon [Giuliano, 1999 #108; Borgstein, 1998 #107]. The main advantage of the technique is that it provides a more cost-effective, less labor-intensive process for focused detection of metastasis, particularly when assessing for the presence of occult tumor cells which are more likely to be associated with earlier disease states [Giuliano, 1998 #15]. The addition of immunohistochemical (IHC) analysis has further improved their identification [Turner, 1999 #17]. The clinical implications of these findings remain to be conclusively determined by historical reviews and therefore prospective multicenter studies are currently underway to evaluate their significance [Wilke, 2003 #51; Grube, 2001 #53]. Regardless, a greater number of patients with small primary tumors are being treated with adjuvant chemotherapy and hormonal therapy. This may be a result of recent studies demonstrating a survival advantage in breast cancer patients without lymph node metastasis [, 1998 #62; 1998 #133; Eifel, 2001 #135]. It must be cautioned that patients with lymph node disease derive the greatest benefit and widespread application of such an aggressive approach may not prove necessary for all cases of early stage breast cancers, as only 20-30% of patients without histopathologic evidence of lymph node metastasis will subsequently develop a recurrence [Winchester, 1991 #61; Cooper, 1991 #58]. Adjuvant chemotherapy is associated with potential for patient toxicity, and its added healthcare costs and resources for its administration must be considered [Hillner, 1991 #59; Smith, 1993 #60]. Consequently, improved methods are needed to better identify patients at increased risk for disease recurrence and systemic metastasis, which would provide a more appropriate utilization of patient care resources.

Breast cancer development is a consequence of a serial accumulation of genetic alterations ultimately resulting in the ability of epithelial cells to proliferate uncontrollably, invade tissues and avoid apoptosis. These genetic events lead to gene activation/inactivation through the mechanisms of mutation, amplification and deletion [Sidransky, 1997 #171]. More recently, it has been shown that different cancers demonstrate significant CpG island hypermethylation in the promoter regions(s) of specific tumor-suppressor and related genes regulating cellular function and contributing to their transcription silencing when compared to normal cells [Baylin, 2001 #66; Esteller, 2001 #65]. These epigenetic events have been suggested to play a significant role in cancer progression [Widschwendter, 2002 #170].

Despite the descriptive profile studies of various genes hypermethylated in breast cancer, relatively little is known of their impact on tumor development and progression [Muller, 2003 #77]. Even more important is whether these tumor genetic aberrations have clinicopathologic utility. In breast cancer where outcome data such as recurrence and survival can only adequately be obtained after a relatively prolonged follow-up period, correlation with established clinical and pathologic prognostic factors may serve as an interim surrogate [Stearns, 2003 #173]. Because lymph node metastasis remains the most significant prognostic factor in patients with early stage breast cancer, we sought to determine whether a hypermethylation marker panel comprising six tumor suppressor and cancer related genes: RAS association domain family protein 1 A protein (RASSF1A), adenomatous polyposis coli (APC), Twist gene of a basic-helix-loop-helix family of transcription factors, E-cadherin (CDH1), glutathione S-transferase pi 1 (GSTP1) and retinoic acid binding receptor-β2 (RAR-β2), detected in primary breast tumors could predict the likelihood of SLN metastasis.

The SLN has been shown to represent the first site of drainage from a primary breast tumor and is most likely to harbor detectable metastasis in patients with early stage disease. Thus, the characterization of an epigenetic tumor profile that is associated with SLN metastasis would not only provide better insight into the biology of breast cancer progression by defining those genetic events associated with the earliest of tumor spreading but may also provide prognostic information from primary tumor assessments. In this study, we developed a methylation-specific PCR (MSP) assay to assess archived paraffin-embedded primary breast tumors for hypermethylation profiles of known tumor-suppressor and related genes with clinicopathologic correlation.

Methods

Patients. A total of 151 patients were identified from the Breast Cancer Database at the John Wayne Cancer Institute who underwent surgery for their primary breast cancer with SLN biopsy alone or with ALND from August 1992 to May 2001. Two thirds of the patients were postmenopausal and mean patient age was 55 years (range: 27-86 years) with a mean tumor size of 3.1 cm (range: 0.1-10 cm). Additional primary tumor characteristics are listed in Table 4. The study was approved by the joint Saint John's Health Center/John Wayne Cancer Institute's institutional review board with all patients providing informed written consent.

TABLE 4

Patient characteristics

| Factors | | n = 151 |
|---|---|---|
| Menopausal | pre | 51 (33.8) |
| | post | 100 (66.2) |
| T Stage | T1a | 1 (0.7) |
| | T1b | 4 (2.6) |
| | T1c | 13 (8.6) |
| | T2 | 118 (78.2) |
| | T3 | 15 (9.9) |
| N Stage | N0 | 71 (47.0) |
| | N1 | 74 (49.0) |
| | N2 | 6 (4.0) |
| M Stage | M0 | 147 (97.4) |
| | M1 | 4 (2.6) |
| AJCC Stage | I | 1 (0.7) |
| | IIa | 86 (57.0) |
| | IIb | 43 (28.5) |
| | IIIa | 17 (11.3) |
| | IV | 4 (2.7) |
| Histology | Ductal | 118 (78.2) |
| | Lobular | 33 (21.8) |
| Differentiation | Well | 30 (20.1) |
| | Moderate | 62 (41.6) |
| | Poor | 57 (38.3) |
| | [Unknown] | [2] |
| Invasion | No | 102 (70.3) |
| | Yes | 43 (29.7) |
| | [Unknown] | [6] |
| SLN status | Negative | 70 |
| | Micro | 40 |
| | Macro | 41 |

DNA Extraction and MSP. Paraffin-embedded primary tumor specimen blocks were sectioned at 10 μm deparaffinized in 100% xylene, followed by 100% ethanol incubation and stained with hematoxylin and eosin (H&E). Tumor tissue was microdissected in comparison to a similarly stained and cover-slipped reference slide cut in sequence from each tissue block. The samples were incubated in buffer containing SDS-proteinase K for 48 hr at 50° C. with an additional 1 μg proteinase K added twice within each 24 hr period. DNA was extracted and bisulfite modification was performed using the agarose bead technique as previously described [Spugnardi, 2003 #86]. Briefly, following extraction, DNA was quantitated using Picogreen (Molecular Probes, Eugene, Oreg.) and 1 μg of genomic DNA was mixed with, 0.3 M NaOH, 2 vols of 2% LMP agarose dissolved in molecular grade water, heated at 80° C. for 10 min and then added to 2-3 drops of chilled mineral oil to create an agarose bead. Sodium bisulfite conversion of DNA suspended in the agarose bead was achieved by adding 2.5 M sodium metabisulfite and 125 mM hydroquinone and incubating at 50° C. for 14 hr. Subsequently, desulphonation was performed by evacuating residual mineral oil and adding 0.2 M NaOH×2 for 15 min each, followed by neutralization with 1/5 vol 1 M HCL for 5 min and then the bead was washed in Tris-EDTA buffer and stored in molecular grade water at 4° C. until analysis. A panel of six genes was assessed for their methylation status: RASSF1A, APC, Twist, CDH1, GSTP1 and RAR-β2. MSP was performed on each bead in a 100 μl reaction containing 200 μM each of dNTP and AmpliTaq Gold DNA polymerase (Perkin Elmer, Norwalk, Conn.) and 50 pmol of each forward (F) and reverse (R) primer set for methylated (M) and unmethylated (U) sets as follows: RAR-β2, (M) F-GAACGC- GAGCGATTCGAGT (SEQ ID NO:1) and R-GACCAATC-CAACCGAAACG (SEQ ID NO:2), (U) F-GGATTGGGATGTTGAGAATGT (SEQ ID NO:3) and R-CAACCAATCCAACCAAAACAA (SEQ ID NO:4); CDH1, (M) F-TTAGGTTAGAGGGTTATCGCGT (SEQ ID NO:5) and R-TAACTAAAAATTCACCTACCGAC (SEQ ID NO:6), (U) F-TAATTTTAGGTTAGAGGGTTATTGT (SEQ ID NO:7) and R-CACAACCAATCAACAACACA (SEQ ID NO:8); APC, (M) F-TATTGCGGAGTGCGGGTC (SEQ ID NO:9) and R-TCGACGAACTCCCGACGA (SEQ ID NO:10), (U) F-GTGTTTTATTGTGGAGTGTGGGTT (SEQ ID NO:11) and R-CCAATCACAAACTCCCAACAA (SEQ ID NO:12); RASSF1A, (M) F-GTGTTAACGCGT-TGCGTATC (SEQ ID NO:13) and R-AACCCCGCGAAC-TAAAAACGA (SEQ ID NO:14), (U) F-TTTGGTTG-GAGTGTGTTAATGTG (SEQ ID NO:15) and R-CAAACCCCACAAACTAAAAACAA (SEQ ID NO:16); GSTP1, (M) F-TTCGGGGTGTAGCGGTCGTC (SEQ ID NO:17) and R-GCCCCAATACTAAATCACGACG (SEQ ID NO:18), (U) F-GATGTTTGGGGTGTAGTGGTTGTT (SEQ ID NO:19) and R-CCACCCCAATACTAAATCA-CAACA (SEQ ID NO:20); Twist, (M) F-TTTCG-GATGGGGTTGTTATCG (SEQ ID NO:21) and R-GAC-GAACGCGAAACGATTTC (SEQ ID NO:22), (U) F-TTGGATGGGGTTGTTATTGT (SEQ ID NO:23) and R-ACCTTCCTCCAACAAACACA (SEQ ID NO:24). PCR was carried out after optimizing annealing temperatures for each primer set to include 40 timed cycles of denaturation at 94° C. for 30 sec, annealing for 30 sec, and extension at 72° C. for 30 sec. Post-MSP product analysis was performed using capillary array electrophoresis (CEQ 8000XL Genetic Analysis System, Beckman Coulter, Fullerton, Calif.) as described previously [Spugnardi, 2003 #86].

Sequencing analysis. Sixteen primary breast tumor samples were randomly selected and analyzed by sequencing to validate the accuracy of the MSP assay for individualized genes. Briefly, PCR was performed on bisulfite modified DNA in 40 µl reactions with forward and reverse primers for specific genes as previously described [Spugnardi, 2003 #86; Hoon, 2004 #176]. Fifteen µl of post-PCR products were resolved on 2% Tris-borate EDTA-agarose gels and target bands were isolated and purified using the Qiagen Gel purification kit (Qiagen Inc., Valencia, Calif.). Sequencing reactions were performed with the dye terminator cycle sequencing kit on the CEQ 8000XL.

Statistical analysis. Descriptive statistics, such as mean, standard deviation, median, frequency and percentage were used to summarize patient's characteristics and gene hypermethylation status. T-test (for continuous variables) and chi-square test (for categorical variables) were used for comparing clinical factors between tumors demonstrating hypermethylation versus no hypermethylation.

A logistic regression model was developed to investigate the correlation of gene methylation status with lymph node metastasis status while the effects of clinical factors on node metastasis were taken into account. First, a stepwise procedure was used to select clinical factors that significantly related with lymph node metastasis status. Tumor size and estrogen receptors status (ER) were selected in the model, a stepwise procedure was used again to select genes that predict node metastasis status. The statistical analysis was carried out using SAS software (SAS, Cary, N.C.) and all tests are two-sided with significant p values ≦0.05.

Results

Promoter region CpG hypermethylation was identified in 147 (97%) of 151 primary breast tumors when evaluated for any one marker using the following panel of genes: RASSF1A, APC, Twist, E-cadherin, GSTP1 and RAR-β2. The most frequently hypermethylated gene detected was RASSF1A occurring in 122 (81%) patients' tumors; this was followed by E-cadherin (53%), APC (49%), Twist (48%), RAR-β2 (24%) and GSTP1 (21%). Forty-five (30%) of 151 tumors demonstrated hypermethylation for three genes, 43 (28%) tumors for two genes, 25 (17%) for four genes, 20 (13%) for one gene, 10 (7%) for five genes, and 4 (3%) for all six genes. In only four patient's tumors, hypermethylation was not detected for any of the six genes assessed. Sequence analysis was performed on 16 primary tumors to verify the hypermethylated or unmethylated status. In all cases, direct sequencing of the PCR product correlated with the methylation status as initially detected by MSP. Ten normal breast tissue samples demonstrated no promoter hypermethylation for any of the genes assessed.

The individual gene hypermethylation status for each patient's tumor was assessed to determine whether any clinical or pathologic correlation could be identified for any of the following prognostic parameters associated with breast cancer: patient's age, menopause status, tumor size, histology, degree of differentiation, DNA index, the presence of lymphovascular invasion, T stage, nodal involvement, AJCC stage, hormone receptor (estrogen and progesterone) status and HER2 receptor presence. GSTP1 methylation was significantly more frequent in primary breast tumors demonstrating lymph node metastasis occurring in 22 (28%) of 81 patients, as compared to 10 (14%) of 70 patients without evidence of lymph node involvement (p=0.044). Hypermethylation of the CDH1 was more frequent in primary tumors demonstrating lymphovascular invasion, 31 (72%) of 43 patients versus 49 (48%) of 102 patient tumors without lymphovascular invasion (p=0.008); those with an infiltrating ductal histology, 68 (58%) of 118 tumors as compared to infiltrating lobular histology 12 (36%) of 33 tumors (p=0.03); and in ER negative tumors, 27 (73%) of 37 patients' tumors versus 53 (47%) of 114 patients' tumors (p=0.005). In contrast, RASSF1A hypermethylation was more frequently associated with ER positive tumors occurring in 99 (87%) of 114 patients versus 23 (62%) of 37 patients with ER negative tumors (p<0.001). RAR-β2 hypermethylation was more common in HER2 positive than negative tumors, 15 (48%) of 31 cases versus 21 (19%) of 112 cases, respectively (p<0.001). No clinical or pathologic correlations were identified for APC or Twist hypermethylation.

In a similar manner, the combination of hypermethylated genes was assessed to determine whether there was any predictive correlation. The presence of hypermethylation for GSTP1 and/or RAR-β2 was more frequently associated with the presence of lymph node metastasis and HER2 receptor positive tumors. Thirty-six (44%) of 81 primary tumors with corresponding lymph node involvement demonstrated hypermethylation for one or both of these markers, whereas this event was only detected in 18 (25%) of 70 primaries without lymph node metastasis (p<0.02). Additionally, hypermethylation for either one or both of these genes was more often found in HER2 positive breast cancers than those that were HER2 negative: 19 (61%) of 31 primary tumors versus 33 (30%) of 112 primary tumors, respectively (p=0.001).

It has been suggested that the amount of regional lymph node involvement is associated with a worse patient prognosis [Rosen, 1981 #99; Nasser, 1993 #98; Goldstein, 1999 #95]. To determine whether hypermethylation profiling of the primary tumor was predictive of lymph node tumor burden, patients were categorized according to the size of the SLN metastasis: macro, >2.0 mm (n=41); micro, ≦2.0 mm (n=40);

and none (n=70), absence of tumor identification following H&E and IHC staining. Among these three groups there was a statistically significant association between increasing SLN tumor burden and larger primary tumor size (p<0.015). Correlation with primary tumor hypermethylation status found a greater frequency of GSTP1 hypermethylation associated with macro-SLN metastasis, 13 (32%) of 41 patients, as compared to those without tumor cells in the SLN, 10 (14%) of 70 patients, p<0.029. RAR-β2 hypermethylation was more common in those tumors having macro-SLN metastasis, 17 (42%) of 41 patients, versus micro-SLN metastasis, 6 (15%) of 40 patients, or no SLN metastasis, 13 (19%) of 70 patients, (p<0.009 for each, respectively). Similarly, the presence of either GSTP1 hypermethylation, RAR-β2hypermethylation, or both was more frequently observed in primary tumors having macro-SLN metastasis, 23 (56%) of 41 patients, than micro-SLN metastasis, 12 (30%) of 40 patients, or no SLN metastasis, 18 (26%) of 70 patients, p values <0.018 and 0.002, respectively.

A logistic regression model was developed to investigate the correlation of gene methylation status with SLN tumor status while the effects of clinical factors on node metastasis were taken into account. Only tumor size and RAR-β2 gene hypermethylation were significantly associated with a greater risk for a macro-SLN metastasis as compared to micro- or no SLN involvement, odds ratio of 1.5 (95% CI, 1.16 to 1.93; p<0.002) and 3.86 (95% CI, 1.65 to 9.00; p<0.002). Similarly, in multivariate analysis, the presence of either GSTP1 hypermethylation, RAR-β2 hypermethylation or both markers in primary tumors correlated with an increased risk of having a macroscopic SLN metastasis, odds ratio 4.59 (95% CI, 2.02 to 10.4; p<0.001). Increasing primary tumor size was also associated with a greater risk for macro-SLN metastasis, odds ratio 1.57 (95% CI, 1.21 to 2.05; p<0.001). No clinical, pathologic or hypermethylation gene marker variables could discriminate between microscopic SLN metastasis and histologically tumor-free SLN.

TABLE 5

Correlation between primary tumor gene hypermethylation marker and patient tumor characteristics

| Gene hypermethylation and tumor histopathology | P-value |
| --- | --- |
| GSTP1 | |
| Lymph node positive | 0.044 |
| CDH1 | |
| Lymph node positive | 0.008 |
| Infiltrating ductal histology | 0.03 |
| Estrogen receptor positive | 0.005 |
| RASSF1A | |
| Estrogen receptor positive | <0.001 |
| RAR-β2 | |
| Her2 receptor positive | <0.001 |
| GSTP1 and/or RAR-β2 | |
| Lymph node positive | <0.02 |
| Her2 receptor positive | 0.001 |

TABLE 6

Correlation between primary tumor gene hypermethylation marker and SLN histology status

| Gene hypermethylation and SLN histopathology | P-value |
| --- | --- |
| GSTP1 | |
| Macro vs. None | <0.015 |
| RAR-β2 | |
| Macro vs. Micro | <0.009 |
| Macro vs. None | <0.009 |
| GSTP1 and/or RAR-β2 | |
| Macro vs. Micro | <0.018 |
| Macro vs. None | <0.002 |

Macro, metastasis >2 mm;
Micro, metastasis ≦2 mm;
None, no metastasis detected by H&E and IHC Discussion Breast cancer remains the most frequently diagnosed malignancy in women [Jemal, 2003 #165], the incidence of which continues to rise yearly. As of lately, many of these detected cases of breast cancer are smaller in size than those reported in previous decades and therefore less likely to be associated with overt lymph node metastasis [Chu, 1996 #8]. Because prospective randomized trials have not demonstrated a survival advantage with up-front ALND, its therapeutic utility in this new era of breast cancer diagnosis will only further diminish [Fisher, 2002 #79]. Regardless, at present, tumor status of the axillary lymph nodes is the single most important clinically used predictor of patient outcome to date [Mansour, 1994 #101]. Furthermore, lymph node evaluation remains a mainstay for disease staging, as a treatment stratification factor, and for assessing overall patient prognosis.

The more frequent utilization of chemotherapy in patients with node-negative breast cancer may further contribute diminishing role of SLN biopsy. In addition there has been a dramatic increase in breast conserving therapy, which entails local radiation. The additional effects of these local and systemic therapies on minimal residual disease in axillary lymph nodes is at present unknown, but may prove beneficial and further reduce the need for lymph node surgery in patients with early stage breast cancer.

Discrimination of primary tumors based on molecular characteristics may prove useful for predicting lymph node metastasis, risk of recurrence, and improving our understanding of the etiologic events that promote disease spreading [Isaacs, 2001 #172]. Advantages of gene-based assays are their rapidity for assessment, widespread use of currently implemented technology, objectivity of results and requirement of only a minimal amount of sample without imposing excessive demands on stringent collection and processing techniques. Additionally, DNA assay studies allow for easy evaluation of available paraffin-embedded tissue specimens. Finally, DNA-based assays offer an alternative to RNA-based approaches, which may be affected by heterogeneity, variations in the levels of gene expression, and most importantly RNA degradation. These factors have proven problematic in large-scale studies.

This study provides the largest series to date with correlation to known prognostic factors in breast cancer to determine the role of gene promoter hypermethylation status as a molecular predictor of disease progression. We found GSTP1 methylation to correlate strongly with increasing tumor size and a greater likelihood of SLN metastasis. This finding is important, as GSTs are a family of enzymes that detoxify hydrophobic electrophiles, which include carcinogens that have been implicated in a variety of cancers [Henderson, 1998 #145]. GSTP1 loss appears to be an early event in the development of prostate cancer and loss of this enzyme may impair cellular defenses leading to increasing genome instability and cancer progression [Nelson, 2002 #141]. Because breast cancer is similarly a hormone mediated malignancy and epidemiologic studies have shown diet and its components as potential contributing factors to its development, this same enzyme may be critical in this disease as well [Clavel-Chapelon, 1997 #142; Krajinovic, 2001 #146]. Additional studies using large-scale populations will better identify these risks and characterize the potential impact of gene-environment interactions.

Hypermethylation of RAR-β2 was shown to correlate more frequently with HER2 positive tumor, which is overexpressed in 25-30% of all breast cancers and when identified is associated with a poorer patient prognosis. Retinoids have been shown to inhibit the growth of breast cancer cell lines in culture and breast tumors in animal models [Lacroix, 1980 #148; Fraker, 1984 #149; Gottardis, 1996 #147]. RAR-β2 has been proposed as a tumor suppressor gene and loss of expression has been found in variety of tumors as well as premalignant lesions resulting in uncontrolled cellular proliferation [Martinet, 2000 #150; Sun, 2002 #151]. Detection of RAR-β2 hypermethylation may identify additional therapeutic targets of interest in these groups of patients with more aggressive tumors. The correlation of RAR-β2 with the presence of macroscopic SLN metastasis is significant. Tumor burden in the lymph nodes is a significant prognosticator of patient outcome. However, the clinical implication of occult tumor cells in lymph nodes remains a controversial issue [Dowlatshahi, 1997 #97; Cote, 1999 #116]. We have demonstrated that patients with SLN micrometastasis ($\leq 2.0$ mm) have equivalent overall survival rate as those without SLN metastasis and both groups have a better outcome than those with SLN macrometastasis (>2.0 mm) [Hansen, 2001 #166]. Genetic markers that predict for lymph node metastasis may avoid further surgery in patients with clinically insignificant disease in their axilla and better identify those more likely to benefit from the addition of systemic therapy. Methylation status of the RAR-β2 may identify patients suitable for enrollment into clinical trials employing retinoids [Lawrence, 2001 #155; Singletary, 2002 #153].

CDH1 hypermethylation was highly associated with ER negative tumors. E-cadherin is involved in cell-to-cell adhesion and the metastasis process. Loss of heterozygosity for this gene with near complete absence of CDH1 protein expression is highly common for invasive lobular breast cancers, whereas tumors of ductal histology often present with varying levels of expression [Asgeirsson, 2000 #158; Cleton-Jansen, 2002 #157]. Promoter region hypermethylation may provide an alternative mechanism to account for this finding in ductal carcinomas.

Promoter region hypermethylation is a common epigenetic event that has been shown to occur among a variety of different tumor types affecting multiple genes that regulate cell cycling, signal transduction, gene transcription, angiogenesis, adhesion and metastasis. Hypermethylation profiling of specific genes in cancers can characterize those genetic alterations associated with tumorigenesis and metastasis [Krassenstein, 2004 #174]. Identification of specific tumor-associated genetic events can potentially account for the pathobiology of tumor progression and provide molecular markers for assessing patient risk, monitoring tumor progression and predicting response to therapy. In addition, this approach allows for the detection of alterations in pathways critical to maintaining cell integrity, stability, survival and chemoresistance which can identify unique patient-specific targets to customize therapies for improved treatment response. Furthermore, development of epigenetic therapeutic protocols may prove useful in the future as preventatives for individuals at high risk for breast cancer. Molecular events associated with the primary tumor that predict for metastasis and patient outcome offers the desired opportunity to avoid additional surgical interventions for staging and will prove more suitable in this new era of earlier cancer detection.

Example 3

Profiling Epigenetic Inactivation of Tumor Suppressor Genes in Tumors and Plasma from Cutaneous Melanoma Patients Introduction Epigenetic events in the form of hypermethylation of TSG promoter region(s) CpG islands can play a role in the development and progression of various cancers (Baylin & Herman, 2000; Esteller et al., 2001; Jones & Baylin, 2002; Sidransky, 2002). The detection of hypermethylated genes in tumors has become important in assessing the mechanisms of known and candidate TSG inactivation. Genes can be transcriptionally silenced when their promoter region(s) CpG islands are hypermethylated (Jones & Baylin, 2002). Recent studies have shown this is a significant mechanism whereby TSG expression is shut off in cancer cells (Baylin & Herman, 2000; Esteller et al., 2001; Jones & Baylin, 2002; Sidransky, 2002). The hypermethylation status of several known or candidate TSG promoter regions has been profiled for a number of cancers (Esteller & Herman, 2002; Harden et al., 2003; Jeronimo et al., 2001; Jones & Baylin, 2002; Lo et al., 2001; Pfeifer et al., 2002; Rosas et al., 2001; Toyooka et al., 2003; Widschwendter & Jones, 2002). This epigenetic regulation of TSG can provide a selective advantage for cells undergoing transformation or progressing to a more malignant phenotype. In the past, considerable effort was devoted to correlating known or candidate TSG deletions and mutations to phenotypic properties. Recent studies have indicated that inactivation of specific TSGs significantly influences tumor promotion and progression in carcinomas (Harden et al., 2003; Jeronimo et al., 2001; Jones & Baylin, 2002; Lo et al., 2001; Rosas et al., 2001; Toyooka et al., 2003; Widschwendter & Jones, 2002).

Most studies on hypermethylation of gene promoter regions have focused on carcinomas; no major study has addressed hypermethylation of TSG in cutaneous melanomas. The genetic mechanisms involved in melanoma tumor progression are poorly understood. BRAF mutation V599 (Davies et al., 2002) and 9p21 region chromosome deletions (Fujiwara et al., 1999) are the major genetic aberrations frequently (>40%) found so far in sporadic primary or metastatic cutaneous melanomas. The frequency of other tumor-related gene mutations or deletions is less than 25% in melanomas. This suggests that there are potential genetic aberrations that have yet to be identified. We recently reported on the frequent hypermethylation (>40%) of RASSF1A in melanoma cell lines and frozen metastatic melanoma specimens (Spugnardi et al., 2003). Although its function remains uncertain, RASSF1A is considered a strong candidate as a TSG.

To date, there has been no major study profiling hypermethylation of known or potential TSGs of cutaneous melanomas. We assessed the hypermethylation status of several known or candidate TSG promoter regions in melanoma cell lines and in frozen and paraffin-embedded melanoma tissues. Several major TSG were frequently hypermethylated in primary tumors and more so in metastatic tumors. Some prominently methylated genes in carcinomas were infrequently methylated in melanomas.

Tumor-related DNA circulates in serum/plasma of patients with melanoma and other types of tumors (Fujiwara et al., 1999; Johnson & Lo, 2002; Sidransky, 2002; Usadel et al., 2002). Studies in melanoma patients have shown that specific microsatellites with loss of heterozygosity (LOH) on different chromosomes are frequent with disease progression (Fujiwara et al., 1999). Recent studies have shown that hypermethylated tumor-related DNA can be detected circulating in blood (Sidransky, 2002; Usadel et al., 2002). We examined the feasibility of detecting hypermethylated TSG in plasma of melanoma patients. Circulating DNA of three hypermethylated genes was demonstrated in plasma of melanoma patients.

Materials and Methods

Cell Lines and Tissues. Fifteen established melanoma cell lines were cultured in growth medium and prepared for DNA extraction as previously described (Fujiwara et al., 1999). Frozen metastatic melanoma tumor specimens (n=53) were obtained from 44 patients who underwent elective surgery at John Wayne Cancer Institute, Saint John's Health Center, Santa Monica, Calif. Frozen tumor-draining lymph nodes (n=10), histopathology tumor negative by immunohistochemistry, were obtained from melanoma patients having elective surgery. Paraffin-embedded metastatic tumor tissues (n=33) and primary tumors (n=20) from melanoma patients were obtained from the Division of Surgical Pathology at Saint John's Health Center. Paraffin-embedded melanoma and breast cancer tumor-draining lymph nodes (n=12) that were histopathology (immunohistochemistry) negative were assessed. For the studies on paired tumors and plasma from the same patients there were additional 24 metastatic tumors assessed; tumors from seven pairs overlapped the initial 86 metastatic patients assessed. All patients had given signed informed consent to participate in the studies. Human subjects IRB approval was obtained for the use of human subjects in this study from Saint John's Health Center and John Wayne Cancer Institute joint committee.

Bisulfite Treatment. DNA was isolated from cell lines and frozen tissues using DNAzol Genomic DNA Isolation Reagent (Molecular Research Center, Inc., Cincinnati, Ohio) according to the manufacturer's recommendations. Paraffin-embedded tumor DNA was extracted as previously described (Fujiwara et al., 1999). Following extraction, DNA was subjected to sodium-bisulfite modification (Spugnardi et al., 2003). One µg of DNA was denatured at 100° C. for 10 min and quickly chilled on ice. Sodium hydroxide (Sigma, St. Louis, Mo.) was then added to a final concentration of 0.3 M, and the DNA incubated at 50° C. for 15 min. The DNA was then mixed with 2 vol 2% LMP agarose (BioWhittaker Molecular Applications, Rockland, Me.) and pipetted into chilled mineral oil, forming a single bead. Four hundred µl of a 5 M bisulfite solution (pH 5.0) consisting of 2.5 M sodium metabisulfite and 125 mM hydroquinone (Sigma) was added, and the reaction incubated at 50° C. for 14 h. The modification was stopped by equilibrating the beads with 0.5 ml 1×Tris-EDTA (TE) (6×15 min) followed by desulphonation using 0.2 M NaOH (500 µl, 2×15 min). The reactions were neutralized using 100 µl (1/5 vol) 1 N hydrochloric acid (Sigma). One final TE rinse was followed by equilibration in molecular grade $H_2O$ (2×15 min). The beads were then used for MSP.

Genomic Sequencing. DNA sequences were amplified by mixing 100 ng of bisulfite treated melanoma cell line DNA with 100 pmoles of each respective primer: MGMT, M1 5'-GGGTTATTTGGTAAATTAAGGTATAGAG-3' (SEQ ID NO:25) and M2 5'-CACCTAAAAATAAAACAAAAAC-TACCAC-3' (SEQ ID NO:26); RASSF1A, R3 5'-GG-GAGTTTGAGTTTATTGAGTTG-3' (SEQ ID NO:27) and R2 5'-CACCTCTACTCATCTATAACCCAAATAC-3' (SEQ ID NO:28); RAR-β2, RA3 5'-GTGTGATAGAAGTAGTAG-GAAGTGAGTTGT-3' (SEQ ID NO:29) and RA2 5'-ACTC-CATCAAACTCTACCCCTTTTTTAAC-3' (SEQ ID NO:30) in a 50 µl reaction containing buffer, of dNTP and AmpliTaq gold polymerase (Applied Biosystems, Foster City, Calif.) at 95° C. for 45 s, 55° C. for 45 s and 72° C. for 2 min for 40 cycles. PCR products were gel purified using the QIAquick Gel Extraction Kit (Qiagen, Valencia, Calif.) and sequenced using an automated DNA sequencer (CEQ 8000XL DNA Analysis System, Beckman Coulter, Fullerton, Calif.) with the respective internal primer: MGMT, M3 5'-GTTGT(c/t)GGAGGATTAGGGT-3' (SEQ ID NO:31); RASSF1A, R4 5'-TACCCCTTAACTACCCCTTCC-3' (SEQ ID NO:32), and RAR-β2, RA4 5'-AATCATAAATTATAACAAA-CAAACCAACT-3' (SEQ ID NO:33).

Fluorescent MSP Analysis. Methylation status was assessed for each gene using two sets of fluorescent labeled primers specifically designed to amplify methylated or unmethylated DNA sequence. Primer sequences are listed as methylated sense and antisense followed by unmethylated sense and antisense, with annealing temperatures and PCR product size: TIMP-3, 5'-CGTTTCGT-TATTTTTTGTTTTCGGTTTC-3' (SEQ ID NO:34) and 5'-CCGAAAACCCCGCCTCG-3' (SEQ ID NO:35) (59° C., 116 bp) 5'-TTTTGTTTTGTTATTTTTTGTTTTTGGTTTT-3' (SEQ ID NO:36) and 5'-CCCCCAAAAACCCCAC-CTCA-3' (SEQ ID NO:37) (59° C., 122 bp) (19); RASSF1A, 5'-GTGTTAACGCGTTGCGTATC-3' (SEQ ID NO:13) and 5'-AACCCCGCGAACTAAAAACGA-3' (SEQ ID NO:14) (60° C., 93 bp), 5'-TTTGGTTGGAGTGTGTTAATGTG-3' (SEQ ID NO:15) and 5'-CAAACCCCACAAACTAAAAA-CAA-3' (SEQ ID NO:16) (60° C., 105 bp) (11,16); RAR-β2, 5'-GAACGCGAGCGATTCGAGT-3' (SEQ ID NO:1) and 5'-GACCAATCCAACCGAAACG-3' (SEQ ID NO:2) (59° C., 142 bp), 5'-GGATTGGGATGTTGAGAATGT-3' (SEQ ID NO:3) and 5'-CAACCAATCCAACCAAAACAA-3' (SEQ ID NO:4) (59° C., 158 bp) (Evron et al., 2001); MGMT, 5'-TTTCGACGTTCGTAGGTTTTCGC-3' (SEQ ID NO:38) and 5'-GCACTCTTCCGAAAACGAAACG-3' (SEQ ID NO:39) (66° C., 81 bp), 5'-TTTGTGTTTTGATGTTTG-TAGGTTTTTGT-3' (SEQ ID NO:40) and 5'-AACTCCA-CACTCTTCCAAAAACAAAAC (SEQ ID NO:41) (66° C., 93 bp) (Esteller et al., 1999); DAPK 5'-GGATAGTCGGATC-GAGTTAACGTC (SEQ ID NO:42) and 5'-CCCTC-CCAAACGCCGA (SEQ ID NO:43) (64° C., 98 bp), 5'-GGAGGATA GTTGGATTGAGTTAATGTT-3' (SEQ ID NO:44) and 5'-CAAATCCCTCCCAAACACCAA-3' (SEQ ID NO:45) (64° C., 106 bp) (Goessl et al., 2000); GSTP1, 5'-TTCGGGGTGTAGCGGTCGTC-3' (SEQ ID NO:17) and 5'-GCCCCAATACTAAATCACGACG-3' (SEQ ID NO:18) (59° C., 91 bp), 5'-GATGTTTGGGGTGTAGTGGTTGTT-3' (SEQ ID NO:19) and 5'-CCACCCCAATACTAAATCA-CAACA-3' (SEQ ID NO:20) (59° C., 97 bp) (Esteller et al., 1999; Zochbauer-Muller et al., 2001); p16$^{INK4a}$, 5'-TTATTA-GAGGGTGGGGCGGATCGC-3' (SEQ ID NO:46) and 5'-GACCCGAACCGCGACCGTAA-3' (SEQ ID NO:47) (65° C., 150 bp), 5'-TTATTAGAGGGTGGGGTGGATTGT- 3' (SEQ ID NO:48) and 5'-CAACCCCAAACCACAAC-CATAA-3' (SEQ ID NO:49) (65° C., 151 bp) (21,24); and MYOD1, 5'-CCAACTCCAAATCCCCTCTCTAT-3' (SEQ ID NO:50) and 5'-TGATTAATTTAGATTGGGTTTA-GAGAAGGA-3' (SEQ ID NO:51) (60° C., 162 bp) (Eads et al., 1999). One hundred ng of bisulfite-modified DNA was subjected to PCR amplification in a final reaction volume of 20 μl containing PCR buffer, 2.5-4.5 mM MgCl$_2$, dNTPs, 0.3 μM primers, BSA and 0.5 U of AmpliTaq gold polymerase (Applied Biosystems). PCR was performed with an initial 10 min incubation at 95° C., followed by 40 cycles of denaturation at 95° C. for 30 s, annealing for 30 s, and extension at 72° C. for 30 s, and a final seven min hold at 72° C. Sodium-bisulfite modified lymphocytes from healthy donors were used as positive unmethylated control, SssI Methylase (New England BioLabs, Beverly, Mass.) treated modified lymphocytes were used as a positive methylated control, and unmodified lymphocytes were used as a negative control for methylated and unmethylated reactions. PCR products were visualized using capillary array electrophoresis (CAE; CEQ 8000XL). The assay was set up in a 96-well microplate format. Multiple PCR products can be assayed in the same well for comparison. Methylated and unmethylated PCR products from each sample were assessed simultaneously by labeling forward primers with a choice of three Beckman Coulter WellRED Phosphoramidite (PA)-linked dyes (Genset Oligos, Boulder, Colo.). Forward methylated specific primer was labeled with D4pa dye and forward unmethylated specific primer was labeled with D2pa dye. One μl of methylated PCR product and one μl of unmethylated PCR product were mixed with 40 μl loading buffer and 0.5 μl dye-labeled size standard (Beckman Coulter Inc). The CAE analysis detects the different dyes and displays them in respective colors.

RT-PCR Analysis. Total cellular RNA was extracted from melanoma cell lines using TriReagent (Molecular Research Center, Cincinnati, Ohio). RT-PCR was performed as previously described (Takeuchi et al., 2003). Briefly, all RT reactions were carried out with oligo-dT priming using 1 μg of total RNA. Resulting cDNA was subjected to PCR conditions of 95° C. for 30 s, annealing for 30 s, and 72° C. for 1 min, for 35 cycles for MGMT, RASSF1A and RAR-β2 and 25 cycles for the GAPDH housekeeping-gene. All samples were assessed for presence of GAPDH mRNA. All PCR products were separated on 2% Tris-borate EDTA agarose gels and stained with ethidium bromide as previously described (Spugnardi et al., 2003).

Reexpression of MGMT, RAR-β2, RASSF1A genes. Several cell lines were grown for four days in T75 cm$^2$ tissue culture flasks in the presence of 0, 3, or 5 μM of 5Aza-dC (Sigma) as previously described (Spugnardi et al., 2003). An additional flask of cells was grown in the presence of 5 μM 5Aza-dC for four days followed by treatment with 1 μM ATRA (Sigma) for 24 h. RNA was isolated and RT-PCR was performed as described above to analyze for RASSF1A, MGMT and RAR-β2 gene reexpression.

Plasma DNA Isolation and Methylation Analysis. DNA was extracted from plasma as previously described (Taback et al., 2001). Briefly, 500 μl of plasma was diluted with 0.9 M NaCl$_2$, SDS, and proteinase K (QIAGEN) and incubated at 50° C. for 3 h. An equal volume of phenol-chloroform isoamyl alcohol (25:24:1) was then added and the sample was vortexed vigorously. After centrifugation at 1000×g for 10 min the aqueous layer was collected and phenol-chloroform isoamyl alcohol was again added. DNA was precipitated using pellet paint NF co-precipitant (Novagen, Madison, Wis.) and isopropanol.

Extracted DNA was subjected to sodium bisulfite modification. Briefly, DNA extracted from 500 μl of plasma and supplemented with 1 μg salmon sperm DNA (Sigma) was denatured in 0.3 M NaOH for 15 min at 37° C. Five hundred fifty μl of a 2.5 M sodium bisulfite/125 mM hydroquinone solution was then added and samples were incubated under mineral oil in the dark for 3 h at 60° C. Salts were removed using the Wizard DNA Clean-Up System (Promega, Madison, Wis.) and samples were then desulfonated in 0.3 M NaOH at 37° C. for 15 min. Modified DNA was precipitated with ethanol using Pellet Paint NF (Novagen) as a carrier and then resuspended in molecular grade H$_2$O.

The methylation status of the bisulfite-treated DNA was determined using primers and probes specifically designed to amplify methylated gene promoter regions. Quantitative RealTime PCR was preformed as previously described (Takeuchi et al., 2003). RealTime PCR reactions were run on the iCycler iQ RealTime thermocycler (Bio-Rad Laboratories, Hercules, Calif.). Analysis involved 25 μL PCR reaction containing sodium bisulfite treated DNA template, 0.8 μM of each primer, 0.4 μM fluorescence resonance energy transfer probe, AmpliTaq gold polymerase (Applied Biosystems), dNTPs, MgCl$_2$, BSA, and AmpliTaq PCR buffer. Amplification conditions were 95° C. for 10 min followed by 55 cycles of denaturation at 95° C. for 1 min, annealing at 60° C. for MYOD1 and RASSF1A (annealing at 59° C. for RAR-β2 and 66° C. for MGMT) and extension at 72° C. for one min. Each PCR plate contained positive controls including melanoma cell lines shown to be methylated for the gene being assessed as well as SssI treated healthy donor lymphocytes. Negative controls included healthy donors plasma DNA and reactions which contained no template DNA.

Realtime PCR assay was performed to obtain the approximate number of methylated gene copies present in a sample. The internal reference gene MYOD1 was used to amplify sodium bisulfite treated DNA independent of methylation status to confirm presence of modified DNA (9). In addition, a standard curve was constructed with serial dilutions of $10^1$ to $10^5$ copies of the targeted TSG promoter region template. Copy numbers for the individual samples were established using the standard curve. Primer sequences for the realtime PCR were the same as for the CAE analysis while the probe sequences were as follows: MYOD, 5'-CCCTTCCTATTC-CTAAATCCAACCTA-3' (SEQ ID NO:52); MGMT, 5'-CGTTTGCGATTTGGTGAGTGTTTGGG-3' (SEQ ID NO:53); RASSF1A, 5'-CAACTACCGTATAAAATTA-CACGCGATACCCCG-3' (SEQ ID NO:54); and RAR-β2, 5'-CCGAATACGTTCCGAATCCTACCCCG-3' (SEQ ID NO:55).

Results

Methylation profiling of melanoma cell lines. Initially, seven known or candidate TSG were assessed for aberrant methylation of CpG promoter regions in melanoma cell lines. Methylation status was analyzed using MSP and assessed by gel electrophoresis initially to verify specific bands. The assay was converted for automated CAE analysis which provided a more objective detection system for methylation status, allowing both methylated and unmethylated MSP products to be assessed simultaneously in the same analysis. A comparison of CAE versus gel electrophoresis demonstrated >95% concordance of results. All subsequent tissue analyses were performed by CAE. The frequency of promoter hypermethylation in the genes DAPK, GSTP1, MGMT, p16$^{INK4a}$, RAR-β2, RASSF1A, and TIMP-3 was assessed by MSP in 15 established melanoma cell lines. The most frequent hypermethylated gene was RASSF1A followed by RAR-β2 and MGMT (Table 7). Overall, 14 (93%) of the lines were hypermethylated for one or more of the seven genes. Eight (53%) cell lines had two or more hypermethylated genes, and two (13%) cell lines had three hypermethylated genes. Positive controls for methylated gene promoter regions included known hypermethylated cell lines and bisulfite-modified SssI treated normal donor PBLs. Negative controls for both methylated and unmethylated primer sets included unmodified (wild-type) DNA and reagent controls. Under the conditions used normal (histopathology tumor negative) frozen lymph nodes (n=10) and healthy donor PBLs did not show methylation for any gene except DAPK, which was positive in PBLs from two healthy donors.

TABLE 7

Methylation of Gene Promoter CpG Islands in Melanoma Cell Lines

| Melanoma cell lines | RAR-β2 | RASSF1A | MGMT | DAPK | GSTP1 | TIMP3 | p16$^{INK4a}$ |
|---|---|---|---|---|---|---|---|
| MA | − | + | − | − | − | − | − |
| MB | − | − | − | − | − | − | − |
| MC | − | + | − | − | − | − | − |
| MD | + | − | + | − | − | − | − |
| ME | + | + | − | − | − | − | − |
| MF | − | + | − | − | − | − | − |
| MG | − | + | − | − | − | − | − |
| MH | + | + | + | − | − | − | − |
| MI | + | + | − | − | − | − | − |
| MJ | + | + | − | − | − | − | − |
| MK | + | + | + | − | − | − | − |
| ML | + | − | − | − | − | − | − |
| MM | + | + | − | − | − | − | − |
| MN | − | + | − | − | − | − | − |
| MO | − | + | + | − | − | − | − |
| Total | 8/15 (53%) | 12/15 (80%) | 4/15 (27%) | 0/15 (0%) | 0/15 (0%) | 0/15 (0%) | 0/15 (0%) |

Figure 1:
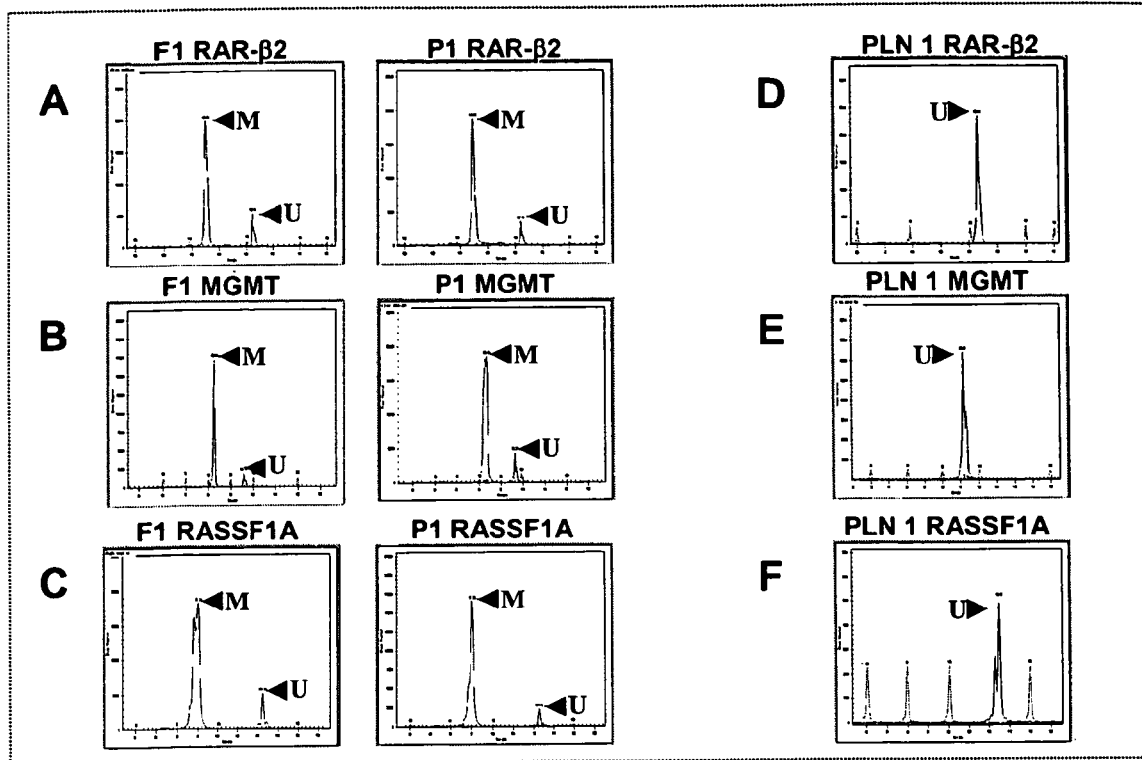
FIG. 1 shows representative examples of paired frozen and paraffin-embedded melanoma tumors analyzed by CAE for determining methylation status of (A) RAR-β2, (B) MGMT, and (C) RASSF1A. Methylated (M) and unmethylated (U) PCR products from frozen (F1) or paraffin-embedded (P1) tumor specimens were analyzed simultaneously and distinguished by size and fluorescence.

Methylation profiling of melanoma tumors. We next assessed 53 frozen metastatic melanoma tumor tissues obtained from 44 AJCC stage III/IV melanoma patients (FIG. 1, Table 8). Hypermethylation was detected in one or more genes of 51 (96%) tumors, two or more genes of 34 (64%) tumors, and three or more genes of 13 (25%) tumors (Table 9). The four most frequently hypermethylated genes were RAR-β2, RASSF1A, MGMT, and DAPK, respectively (Table 8). The other three genes were hypermethylated in less than 10% of the tumors.

TABLE 8

Detection of Hypermethylated Genes in Melanoma Tumors

|  | MGMT | RAR-β2 | RASSF1A | DAPK |
|---|---|---|---|---|
| Primary tumors |  |  |  |  |
| Paraffin n = 20 | 2 (10) | 14 (70) | 3 (15) | 0 (0) |
| Metastatic tumors |  |  |  |  |
| Frozen n = 53 | 20 (38) | 38 (72) | 31 (58) | 13 (25) |
| Paraffin n = 33 | 9 (27) | 22 (67) | 18 (55) | 3 (9) |
| Total n = 86 | 29 (34) | 60 (70) | 49 (57) | 16 (19) |

( ) percentage

TABLE 9

Frequency of Hypermethylated Genes in Melanoma Tumors

|  | Genes$^a$ | Frozen n = 0 | Paraffin n = 20 | Total |
|---|---|---|---|---|
| Primary tumors | 0 | N/A | 5 (25) | 5 (25) |
| N = 20 | ≧1 | N/A | 15 (75) | 15 (75) |
|  | ≧2 | N/A | 4 (20) | 4 (20) |
|  | ≧3 | N/A | 0 (0) | 0 (0) |

TABLE 9-continued

Frequency of Hypermethylated Genes in Melanoma Tumors

|  | Genes* | Frozen n = 53 | Paraffin n = 33 | Total |
|---|---|---|---|---|
| Metastatic tumors | 0 | 2 (4) | 1 (3) | 3 (3) |
| N = 86 | ≧1 | 51 (96) | 32 (97) | 83 (97) |
|  | ≧2 | 34 (64) | 17 (52) | 51 (59) |
|  | ≧3 | 13 (25) | 3 (11) | 16 (19) |
|  | 4 | 4 (8) | 0 (0) | 4 (5) |

( ) percentage
$^a$Genes assessed were: RAR-β2, MGMT, DAPK, and RASSF1A.

Because molecular assessment of frozen tumor tissues is hampered by availability, size of lesion surgically removed, logistics of tissue procurement, not knowing the level of contamination with hemopoietic cell infiltrates and normal cells, the MSP assay was adapted for analysis of paraffin-embedded tumor tissue. We focused on the four genes most frequently hypermethylated in frozen melanomas: RAR-β2, RASSF1A, MGMT, and DAPK. We initially assessed 11 paired frozen and paraffin-embedded melanomas to verify that the sensitivity of the assay was equivalent for both types of tissues. There was 100% concordance for all four markers between frozen and paraffin-embedded melanomas.

Primary melanomas were assessed only from paraffin-embedded tissues opposed to fresh frozen tissues due to the lesion size, and logistics in procurement for pathology analysis. Paraffin-embedded primary melanomas (n=20) and metastatic melanomas (n=33) were assessed (FIG. 1, Table 8). The most frequently hypermethylated genes for primary tumors were RAR-β2, RASSF1A, and MGMT, respectively. Surprisingly, RAR-β2 was hypermethylated in 70% of the primary tumors. Fifteen (75%) tumors had one or more genes methylated, and only four (20%) had two or more genes methylated. Of the metastatic tumors 32 (97%) had one or more genes methylated, and 17 (52%) had two or more genes methylated (Table 9). Overall, metastatic tumors had a higher frequency of hypermethylated genes. Paraffin-embedded histopathology tumor-negative lymph nodes (n=12) were negative for hypermethylation of RAR-β2, RASSF1A, and MGMT (FIG. 1). Analysis of the combination of metastatic (frozen and paraffin-embedded) melanoma tumors (n=86) is shown in Table 9. There was no significant association of hypermethylation between any individual genes, nor was gene hypermethylation correlated with disease outcomes. However, RAR-β2 significantly (p=0.009) correlated with primary tumor Breslow thickness. This correlation is important in that Breslow thickness is a major prognostic factor in early stage melanoma patients with localized disease.

Gene reexpression by demethylation. Expression of MGMT, RASSF1A, and RAR-β2 was assessed in eight melanoma cell lines by RT-PCR. No gene transcripts were detected in cell lines exhibiting hypermethylation. Gene expression was detected in the non-methylated cell lines and in some partially hypermethylated cell lines.

Melanoma cell lines that were hypermethylated were treated with the DNA methylation inhibitor 5Aza-dC to reverse epigenetic transcriptional silencing caused by methylation (16). Melanoma cell lines were treated with 0, 3, and 5 µM of 5Aza-dC for four days. Treatment with 5Aza-dC induced significant elevation of gene expression in all methylated cell lines, of which mRNA expression for was absent or very minimal prior to drug treatment (FIG. 2). Melanoma cell lines exhibiting no hypermethylation of the gene promoter region for MGMT and RASSF1A demonstrated significant elevation of mRNA levels. For assessment of hypermethylated RAR-β2 in cell lines, cells were treated with 5Aza-dC for four days followed by treatment with 1 µM ATRA for 24 h. Methylation was reversed in all treated cell lines and RAR-β2 mRNA expression elevation was detected. Cell lines demonstrating hypermethylated product by MSP showed no mRNA expression. For some of the genes in the cell lines, there was moderate to low levels of hypermethylated product produced by MSP with minimal gene expression before drug treatment. Gene expression was significantly elevated in all cell lines after drug treatment. These in vitro studies are suggestive that hypermethylation of the promoter region of the genes assessed is an active mechanism of silencing gene expression.

Bisulfite sequencing was carried out on multiple cell lines to confirm the methylation status of MGMT, RASSF1A, and RAR-β2 CpG island promoter regions and confirm the MSP results. Representative examples of sequencing is shown in FIG. 3. Sequencing and MSP of individual gene hypermethylation were concordant.

Analysis of circulating methylated DNA in plasma. We examined the presence of methylated DNA circulating in plasma of melanoma patients using realtime PCR. A realtime MSP assay was developed for detection of methylated DNA in plasma because the level of DNA is significantly lower in plasma than tissues. An assay using a reference gene (MYOD1) and standard curves for individual markers was developed to assess realtime MSP results. The average DNA recovered from normal donor controls was 18.15 ng DNA/500 µl (range 5.31-42.92) and from melanoma patients 29.24 ng DNA/500 µl (range 9.97-166.87). In this study, we assessed RAR-β2, RASSF1A, and MGMT, the three genes most frequently hypermethylated in tumors. Thirty-one AJCC stage III/IV patients in whom we had paired plasma and melanoma tumor tissues comprised the study group. Selection was based on availability of paired samples. Plasma was obtained from a preoperative blood specimen. The most frequently methylated gene in plasma was RASSF1A (n=6; 19%) followed by MGMT (n=6; 19%) and RAR-β2 (n=4; 13%). Of the 31 patients, 29% had at least one gene hypermethylated and 16% of the patients had a least two genes hypermethylated in their plasma. Plasma from 33 healthy normal donors was negative for hypermethylation of all three genes. Analysis of methylation for MYOD1 gene was run on all samples for verification of modification and detection of DNA. Concordance of plasma gene hypermethylation status to respective paired tumors was as follows: MGMT (6 of 17; 33%); RASSF1A (5 of 20; 24%); and RAR-β2 (4 of 20; 18%). This suggests that there may be degradation or limited release of these DNA markers. In two patients, hypermethylation of RASSF1A was absent in tumors but present in plasma. This may be due to other metastases not surgically excised or subclinical disease. These preliminary studies suggest hypermethylated genes can be detected in accellular plasma of melanoma patients. Further detailed studies will validate the clinical utility of these DNA markers.

Discussion

Hypermethylation of gene promoter regions silences genes in many types of carcinomas. Profiling studies have shown gene hypermethylation frequency and specific genes for tumors of different histological origins (Chen et al., 2003; Esteller et al., 2001; Maruyama et al., 2001; Pfeifer et al., 2002; Toyooka et al., 2003; Widschwendter & Jones, 2002). Patterns of gene hypermethylation in primary tumors versus metastases, and their association with clinicopathological factors are not well described. However, there is clear indication that hypermethylation of TSG promoter regions is a significant mechanism by which gene transcription is turned off in cancer cells. Studies of tumor cell lines may not be accurate as to the actual frequency of hypermethylation of gene promoter regions in tumor specimens (Paz et al., 2003; Smiraglia et al., 2001; Ueki et al., 2000). Hypermethylation of specific genes in cell lines may represent clonal selection during culture adaptation and passaging. Our major finding is that hypermethylation of promoter regions of known and candidate TSGs in melanomas is quite frequent. Hypermethylation of a gene can be potentially used as a surrogate of altered gene expression patterns to characterize phenotypic behavior.

At least one of seven genes was hypermethylated in 93% of cell lines, a frequency that suggest a relation between hypermethylation and melanoma progression. The study demonstrated that several frequently methylated TSGs in carcinomas were also found in primary and metastatic cutaneous melanomas. Interestingly, the three genes most commonly hypermethylated in cell lines, two were slightly more hypermethylated and one was more hypomethylated in metastatic tumors. Recent studies have reviewed the comparison of cell lines and tumors and have come up with different conclusions (Paz et al., 2003; Smiraglia et al., 2001; Ueki et al., 2000). However, one has to be careful in comparing cell lines to tumors; an important consideration is whether the tumor is a primary or metastatic lesion or one of multiple lesions. In our study, hypermethylation was less marked in primary tumors compared to cell lines and metastases. One exception was RAR-β2 where both primary and metastatic tumors demonstrated higher levels of hypermethylation than cell lines.

RAR-β2 was the most frequent hypermethylated gene in the panel of seven genes assessment. This is the first major report in describing hypermethylation of RAR-β2 in melanoma in a large series of tumor specimens. Previous studies have demonstrated the frequent hypermethylation of this gene in breast and lung carcinomas (Paz et al., 2003; Sirchia et al., 2002; Widschwendter et al., 2000). RAR-β2 is a member of the nuclear retinoid receptor of genes, family referred to as retinoic acid receptors (RAR) (Mangelsdorf & Evans, 1995), which are frequently turned off or not expressed in a number of carcinomas. The loss of RAR-β2 has been implicated in tumorigenesis. Interestingly, the frequency (70%) of RAR-β2 hypermethylation was similar among primary and metastatic tumors. This is one of the highest frequencies of genetic aberration reported for sporadic primary melanomas. BRAF mutation in primary tumors is about 31% (Shinozaki et al; unpublished data). The inhibition of transcription of RAR-β2 may be a key factor in sporadic cutaneous melanoma tumor development. RAR-β loss has been demonstrated as a biomarker of bronchial preneoplasia (Kurie et al., 2003). We demonstrated a significant correlation between hypermethylation of RAR-β2 and increasing primary tumor Breslow thickness which is a major prognostic factor for early-stage melanoma (Bostick et al., 1999). Silencing of RAR-β2 may be a key epigenetic factor in melanocyte transformation and primary lesion progression. Further studies are needed to identify RAR-β2 loss during melanocyte and nevus transformation to melanoma.

Retinoic acid treatment can induce differentiation and inhibition of proliferation in selective melanoma cells (Demary et al., 2001). The variable responsiveness of melanomas has not been understood. It has also been shown that retinoic acid can activate RAR-β receptors (Spanjaard et al., 1997). Further studies may be warranted to examine strategic molecular targeting of therapeutics based on RAR-β status in melanoma.

The second most frequently hypermethylated gene was RASSF1A. This larger study supported our previous report that RASSF1A is frequently methylated in metastatic melanomas (Spugnardi et al., 2003). The 42% higher rate of RASSF1A hypermethylation in metastatic versus primary tumors suggests that hypermethylation of RASSF1A is likely to be acquired during tumor progression. Few published studies have compared hypermethylation of genes in primary and metastatic tumors of the same tumor type. The functional role of RASSF1A is still not clear. However, its inactivation as a TSG in multiple types of cancers has been demonstrated (Dammann et al., 2000; Dammann et al., 2001; Lo et al., 2001; Pfeifer et al., 2002; Spugnardi et al., 2003).

The third most commonly gene hypermethylated gene was MGMT; its rate of hypermethylation was 24% higher in metastases than in primary tumors. MGMT, a DNA repair gene, serves as a key regulator of genome integrity. Studies have shown that MGMT expression protects mammalian cell lines from spontaneous G:C to A:T transitions (Christmann et al., 2001). Melanoma is known to have acquired resistance to antineoplastic agents such as alkylating drugs exhibiting methylating and chlorethylating properties such as dacarbazine, procarbazine, and temozolomide (Christmann et al., 2001). The overall frequency of DAPK, p16$^{ink4a}$ and GSTP1 gene often found hypermethylated in carcinomas, was quite low in melanoma. The three major genes we assessed were frequently hypermethylated in both primary and metastatic melanomas. There are likely other TSGs and tumor-related genes inactivated through hypermethylation during melanoma progression. A more global screening approach is needed such as DNA methylation microarray analysis (Shi et al., 2003) that will allow assessment of multiple genes for multiple specimens.

Previously, we have demonstrated circulating DNA in plasma in the form of LOH of microsatellites in melanoma patients (Fujiwara et al., 1999; Taback et al., 2001). In the present study, we demonstrated that melanoma patients have circulating hypermethylated DNA in their plasma. The three most common genes in melanoma tumors were detected in plasma at a lower frequency. A quantitative realtime PCR assay was developed to improve sensitivity and accuracy of methylated DNA in plasma. The assay was 100% specific as no normal donors' plasma under the assay conditions was positive. Future studies need to optimize the assay to obtain high sensitivity for early disease diagnosis. This is the first major study demonstrating the presence of a significant number of melanoma patients with circulating methylated DNA markers. The half-life of individual genes will play a significant role as to the value of detection of these circulating DNA. Circulating methylation DNA markers may be used as surrogates of subclinical disease recurrence or progression. Detailed studies on larger cohorts of patients are needed to determine whether these circulating methylation markers have clinical utility in predicting disease outcome. Nevertheless, it is intriguing that circulating methylated DNA is present in plasma and released by tumor cells. Whether this DNA is from established metastases or circulating tumor cells in blood needs to be determined. Further studies on defined cohorts of melanoma patients need to be studied to determine the potential clinicopathological utility in assessment of melanoma patients plasma for circulating DNA.

Example 4

Prognostic Significance of Hypermethylated Tumor Suppressor Genes in Metastatic Melanomas Introduction Hypermethylation (HM) of CpG islands of promoter regions of tumor suppressor genes (TSG) silences gene expression and promotes tumor progression. Among AJCC stage III melanoma patients who have palpable nodes and undergo complete lymph node dissection (CLND), there are patients who have better prognosis than others even when matched for prognostic factors. We have discovered that the TSG RAS association domain family protein 1 (RASSF1A) and retinoic acid receptor β2 (RARB) are HM in cutaneous melanomas. We hypothesized that regional lymph node metastasis with HM TSGs is predictive of a poorer disease outcome.

Methods

AJCC stage III melanoma patients (n=37) who underwent CLND with palpable nodes were selected by the biostatistician. HM of the promoter regions of RASSF1A and RARB using quantitative realtime methylation-specific PCR from DNA isolated of paraffin-embedded metastatic tumors was analyzed. Genomic copy numbers of gene methylation were normalized and quantified with copy numbers of the MYOD gene.

Results

The study group consisted of 10 females and 27 males (mean age 55.7 yrs; mean Breslow thickness 2.32 mm±1.46). Primary lesions were located on the trunk (14), extremities (15), head and neck (5), or an unknown site (3). All patients had at least 2 palpable nodes (mean 11.4; range 3-33). HM was detected for RASSF1A alone (16%), RARB alone (28%), and both TSGs (14%). HM RARB alone correlated with overall survival and disease-free survival by multivariate analysis, Wald test; p=0.008 and p=0.009, respectively. The median overall survival was 27.7 mos for nonHM RARB vs 9.5 mos for HM RARB. The median disease-free survival was 8.5 mos for nonHM RARB vs 3.9 mos for HM RARB. RARB did not correlate with any of the 7 prognostic factors.

Conclusions

HM of RARB in regional lymph node metastasis has prognostic significance in prediction of disease outcome in melanoma patients. This pilot study demonstrates that epigenetic inactivation of TSG can be used as genomic predictive marker of disease outcome.

Example 5

Blood, Bone Marrow, and Tumor Markers for Various Types of Cancer

Materials and Methods

BM Sample Preparation. Bone marrow was drawn and (cell-free supernatant) plasma was immediately separated by centrifugation (1000×g, 15 min), filtered through a 13-mm serum filter (Fisher Scientific, Pittsburgh, Pa.) to remove any potential contaminating cells, aliquoted and cryopreserved at −30° C. For normal genomic DNA controls, whole blood was collected from each patient spotted and stored on FTA blood cards (Fitzco, Minneapolis, Minn.) prior to DNA isolation. DNA was extracted from one ml of BM aspirate plasma using QIAamp extraction kit (Qiagen, Valencia, Calif.) using conventional methods[23].

Preparation of Samples from Primary Tumor Tissues and LOH Analysis of the Obtained Samples. DNA was isolated from 10 μm sections cut from paraffin-embedded tumor tissue blocks. Samples were deparaffinized and microdissected using laser capture microscopy (Arcturus, Mountain View, Calif.) from normal tissue. Microdissection may also be carried out using a scalpel or needle and a microscope or a precision laser cutting instrument. Then, DNA was isolated, processed, purified, and quantitated.

For example, in one study, DNA was isolated by incubating the samples with proteinase K in lysis buffer (50 mM Tris-HCl, 1 mM EDTA and 0.5% Tween 20) at 37° C. overnight and then heated at 95° C. for 10 min. The obtained samples were amplified and analyzed for LOH using PCR methods. The amplification/detection methods used were PCR and gel electrophoresis using labeled primers (fluorescent or radioactive); RealTime PCR using specific labeled primers Taqman and probes (labeled with chromatographic dyes); or capillary array electrophoresis (CAE) with labeled PCR primers (no probes). All of these methods are known to those skilled in the art and will not be described here in detail.

LOH Analysis in Blood and BM Samples. LOH analysis of blood (plasma/serum) and bone marrow were performed as described in papers by B. Taback[24] and Y. Fujiwara[27], the content of which is incorporated herein by the reference. DNA was isolated, processed, purified, and analyzed for the presence of LOH as generally described in B. Taback[24] and Y. Fujiwara[27] references. The isolation procedure was the same regardless the type of cancer (breast, melanoma, prostate, colon cancer) being detected.

The amplification/detection methods used were PCR and gel electrophoresis using labeled primers (fluorescent or radioactive); RealTime PCR using specific labeled primers Taqman and probes (labeled with chromatographic dyes); or capillary array electrophoresis (CAE) with labeled PCR primers (no probes). All of these methods are known to those skilled in the art and will not be described here in detail.

Methylation Analysis of Blood, BM, and Tumor Tissue Samples. The samples of blood, BM, and tumor tissue were prepared as the samples for LOH analysis. Then, the samples were treated with bisulphite and proteinase K to separate out methylated from unmethylated DNA. Methylation specific PCR (MSP) was performed. A more detailed description of this method follows.

DNA was isolated from cell lines and tissues using DNAzol Genomic DNA Isolation Reagent (Molecular Research Center, Inc., Cincinnati, Ohio) according to the manufacturer's recommendations. The methylation status of the marker promoter region was determined by a bisulfite modification protocol[60,61]. Briefly, 1 mg of genomic DNA was denatured in NaOH at 37° C. Cytosines were sulfonated in the presence of sodium bisulfite and 5 mM hydroquinone (Sigma) in a water bath for 16-18 h at 55° C. The DNA samples were desalted using the Wizard DNA Clean-Up System (Promega, Madison, Wis.) and desulfonated in NaOH at 37° C. Treated DNA samples were precipitated with ethanol and resuspended in 10 mM Tris-Cl, 1 mM EDTA, pH 7.6. DNA sequences were amplified by mixing 100 ng of bisulfite treated DNA with 50 pmoles of individual primer sets; reaction buffer containing each dNTP and Taq polymerase at 95° C. for 1 min, 55° C. for 1 min and 74° C. for 2 min for 30 cycles.

For MSP (methylation specific PCR), two methods were used to assess the different regions of the marker CpG promoter island. In the first method, PCR was performed and assessed on 2% Tris-borate EDTA agarose gel. In the second method, one hundred ng of bisulfite-modified DNA was amplified in a final reaction volume of 20 ul containing 0.8 mM dNTPs, and Taq polymerase. PCR was performed with an initial 10 min incubation at 95° C., followed by 40 cycles of denaturation at 95° C. for 30 sec, annealing at 60° C. for 30 sec, and extension at 72° C. for 30 sec, and a final 7 min hold at 72° C. PCR products were visualized using capillary array electrophoresis (CAE; CEQ 2000XL DNA Analysis System, Beckman Coulter, Fullerton, Calif.).

The assay was set up in a 96-well microplate format. Multiple PCR products can be run in each well for comparisons. Multiple PCR products were visualized simultaneously by labeling forward primers with a choice of three Beckman Coulter WellRED Phosphoramidite (PA)-linked dyes. Forward methylated specific primer was labeled with D4pa dye (blue) and forward unmethylated specific primer was labeled with D2pa dye (black). One ml of methylated PCR product and one ml of unmethylated PCR product were mixed with 40 ml loading buffer and 0.5 ul dye-labeled size standard (Beckman Coulter Inc.). Labeling forward primers specific for methylated or unmethylated modified DNA distinguishes the respective products so that they may be analyzed simultaneously. Other methods for detection of methylation markers, such as ligase PCR and Realtime PCR with specific marker probe, may also be used.

Methylation Site Sequencing to Prove the Marker's Site is Methylated. Bisulfite sequencing was carried out to confirm the methylation status of the CpG island promoter region, which regulates the marker gene transcription. Extracted DNA was treated with sodium bisulfite, which converts unmethylated cytosines to uracil. Thymine is then substituted for uracil during subsequent PCR. Methylated cytosines (5-methylcytosine) are protected from this process and remain unchanged. Accordingly, all cytosines present following sequence analysis represent methylated cytosines. All markers used for methylation were confirmed by methylation sequencing.

Results

Determining LOH in the BM of Breast Cancer Patients. BM aspirates were collected in 4.5 ml sodium citrate tubes (Becton Dickinson, Franklin Lakes, N.J.) through bilateral anterior iliac approach from 48 consecutive patients as follows: ductal carcinoma in situ (DCIS), 1 patient; American Joint Committee on Cancer (AJCC) stage I, 32 patients; AJCC stage II, 13 patients; and AJCC stage III, 2 patients; undergoing surgical resection of their primary breast cancer at the Saint John's Health Center/John Wayne Cancer Institute. In addition, five healthy female volunteer donors contributed BM aspirate samples for controls. To assess the correlation of LOH found in the BM and that of the primary breast tumor, DNA was isolated from 10 μm sections cut from paraffin-embedded tumor tissue blocks. Additionally, each BM aspirate was assessed for the presence of occult tumor cells by conventional histologic staining methods using Hematoxylin and Eosin (H&E).

Eight polymorphic microsatellite markers which correspond to regions that have been shown to demonstrate significant LOH suggesting sites of putative tumor suppressor and/or metastasis related genes were selected: D1S228 at 1p36; D8S321 at 8qter-8q24.13; D10S197 at 10p12; D14S51 at 14q32.1-14q32.2; D14S62 at 14q32; D16S421 at 16q22.1; D17S849 at 17pter-17qter, and D17S855 at 17q. All primer sets were obtained from Research Genetics (Huntsville, Ala.) and sense primers were labeled with a fluorescent dye: 5-(and-6)-carboxyfluoroscein, FAM.

Approximately 20 ng of genomic DNA was amplified by PCR in 25 μl reactions containing 1×PCR buffer (Perkin Elmer, Foster City, Calif.), 6 pmol of each primer, 1 unit of Taq DNA polymerase, 2.5 μM deoxynucleotide triphosphates, and 1.5 mM $MgCl_2$. Forty PCR cycles were performed with each cycle consisting of 30 s at 94° C., 30 s at 50-56° C., and 90 s at 72° C., followed by a final extension step of 72° C. for 5 min as previously described[23].

PCR products were electrophoresed on 6% denaturing polyacrylamide gel containing 7.7 M urea at 1600V for 2 h. Genomyx SC scanner (Beckman Coulter, Fullerton, Calif.) was used to image the fluorescent-labeled PCR products and densitometric analysis was performed with ClaritySC software (Media Cybernetics, Silver Spring, Md.). Intensity calculations and comparisons of the specific alleles in patients' normal control and respective BM DNA were performed to evaluate for LOH. The LOH was defined if a greater than 50% reduction of intensity was noted in one allele from tumor or BM DNA when compared with the respective allele in the matched-paired lymphocytes[23].

Clinical and histopathologic data was obtained from patient chart review and the Breast Tumor Registry at the John Wayne Cancer Institute. Chi-Square and Wilcoxon Rank Sum tests were performed for statistical evaluation of association of BM LOH status and known prognostic parameters.

LOH was identified in 11 (23%) of 48 patients' BM aspirates. LOH was most commonly identified at microsatellite marker D14S62 occurring in 4 (12%) of 34 informative patients. Microsatellite markers demonstrating LOH at D1 S228 and D14S51 occurred in 3 (8%) of 38 informative patients each, followed by LOH at D8S321 (5%), D10S197 (4%), and D17S855 (3%). No LOH was detected for microsatellite markers D16S421 and D17S849 (Table 10). Eight of the 11 patients with detectable LOH in their BM demonstrated this event at only one of the chromosome loci assessed and three patients (1 stage I, 2 stage II patients) contained LOH for two microsatellite markers. No LOH was detected for any of the microsatellite markers assessed in the patient with DCIS or the BM aspirates collected from five healthy female donors.

TABLE 10

LOH Frequency in Breast Cancer Patients

| Bone Marrow Aspirates Microsatellite marker | LOH in BM aspirates/ informative cases (%) |
| --- | --- |
| D14S62 | 4/34 (12%) |
| D14S51 | 3/38 (8%) |
| D1S228 | 3/38 (8%) |
| D8S321 | 2/39 (5%) |
| D10S197 | 1/26 (4%) |
| D17S855 | 1/37 (3%) |
| D17S849 | 0/31 (0%) |
| D16S421 | 0/28 (0%) |

The inventors found LOH on chromosome 14q as the most frequent event identified on circulating DNA in BM. However, in another study, LOH on 14q has been shown to occur more commonly in primary tumors without lymph node metastasis, suggesting a site for a possible metastasis-related gene; however, the metastasis itself was not assessed for LOH[43]. While not wanting to be bound by a theory, the inventors believe that metastatic clones at different sites may demonstrate different LOH profiles. Additionally, differences in these results may reflect the stability of this marker as detected from various sources (blood, BM, tumor tissues) or it may be uniquely associated with site-specific metastasis. Molecular markers that are specific for the metastatic phenotype and/or sites of metastasis may prove useful for focusing clinical assessments.

There was an increased association between the presence of LOH in the BM and advanced disease stage. Six (19%) of 32 AJCC stage I patients demonstrated LOH for at least one marker, in contrast to 4 (31%) of 13 AJCC stage II patients, and 1 (50%) of 2 AJCC stage III patients (Table 11).

TABLE 11

Association of LOH in Patients' BM Aspirates with AJCC Stage

| AJCC Stage | Patients with LOH in BM/ total patients (%) |
| --- | --- |
| I | 6/32(19%) |
| II | 4/13(31%) |
| III | 1/2 (50%) |

Ten clinicopathologic prognostic factors were assessed for correlation with BM LOH status: histologic tumor type, size, grade, Bloom-Richardson score, lymph node involvement, presence of lymphovascular invasion in the primary tumor, receptor status (estrogen, progesterone, HER2), and p53 status. There was an association between larger tumor size and BM LOH positivity: 2.46 cm versus 1.81 cm, mean tumor sizes, respectively. There was also a trend towards an increased incidence of BM LOH in lymph node positive patients as compared with lymph node negative patients: 3 (33%) of 9 patients versus 8 (21%) of 38 patients, respectively. No significant correlation existed between any prognostic factor and BM LOH status in this study except histology. Lobular carcinomas were more likely associated with increased LOH in BM aspirates than infiltrating ductal tumors: 6 (60%) of 10 patients versus 5 (14%) of 37 patients, respectively (Chi-Square test P=0.006). Larger populations with long-term follow-up are warranted to evaluate the clinical and prognostic utility of this assay.

To determine whether a correlation existed between the LOH detected in patients BM and their primary tumor, DNA was isolated from primary tumors and evaluated with identical microsatellite markers. Ten of the eleven patients demonstrating LOH in their BM had primary tumors available for assessment. In all ten patients, the LOH identified in the BM was also present respectively in the primary tumor (FIG. 4). Conventional histological analysis of all specimens using standard H&E staining did not demonstrate occult tumor cells in any of the BM samples.

Determining LOH and CpG Hypermethylation in Blood (Serum/Plasma) of Prostate Cancer Patients. To evaluate the clinical utility of assessing circulating nucleic acids containing tumor-associated genetic alterations in serum/plasma of prostate cancer, patients' blood was collected from 23 prostate cancer patients American Joint Committee on Cancer (AJCC) stages I-IV. A panel of 7 microsatellite markers (D8S261, D8S262, D9S171, D10S591, D10S532, D16S422 and D18S70) on 6 chromosome arms pertaining to putative tumor suppressor gene regions was utilized to assess prostate cancer patient's serum/plasma for LOH on circulating nucleic acids.

In addition, methylation specific PCR and capillary array electrophoresis was performed on the same samples to evaluate the presence of CpG island hypermethylation in the promoter regions of three known tumor suppressor genes: RASSF1A, RAR-β and GSTP1. The obtained results are shown in Table 12 below.

TABLE 12

Association of LOH and Methylation in Prostate Cancer Patients' Blood Samples with AJCC Stage

| AJCC Stage | Methylation | LOH | Molecular Positive (%) |
|---|---|---|---|
| I | 0/3 | 0/3 | 0% |
| II | 0/5 | 2/5 | 40% |
| III/IV | 8/15 | 5/15 | 60% |

A correlation of an increased combination of promoter region hypermethylation and LOH identified on circulating nucleic acids was associated with advancing AJCC staging. The incidence of LOH increased from 2 (25%) of 8 stage I-II patients to 5 (33%) of 15 stage III-IV patients. None of the early stage patients demonstrated methylated DNA in their blood whereas 8 (53%) of 15 stage III-IV patients where positive for any one methylated marker in their blood. Although, it appears that testing blood for hypermethylation or LOH alone may be used to detect and diagnoses prostate cancer, testing for both hypermethylation and LOH may provide a higher sensitivity and accuracy in detection and determination of the AJCC stage of prostate cancer.

Determining LOH and CpG Hypermethylation in Blood (Serum/Plasma) of Colorectal Cancer Patients. To evaluate the presence of circulating nucleic acids containing tumor-associated genetic alterations in serum/plasma of colorectal cancer patients, blood was collected from 33 colorectal cancer patients undergoing surgical resection for their primary diagnosis. A panel of 11 microsatellite markers (D4S175, D4S1586, D5S299, D8S133, D8S264, D15S127, TP53, D17S796, D17S1832, D18S58 and D18S61) on 6 chromosomes at loci demonstrating frequent LOH in primary colorectal tumors suggestive of putative tumor suppressor gene regions were utilized. In addition, methylation specific PCR and capillary array electrophoresis was performed on the same samples in 16 patients to evaluate the presence of CpG island hypermethylation in the promoter regions of five known tumor suppressor genes: MGMT, P16, APC, RASSF1A and RAR-β. The obtained results are shown in Tables 13 and 14 below.

TABLE 13

Frequency of Microsatellite Marker LOH in Colorectal Cancer Patients' Blood

| D18S58 | D18S61 | TP53 | D17S1832 | D5S299 | D4S175 | D4S1586 | D8S133 | D8S264 | D15S127 | D17S796 |
|---|---|---|---|---|---|---|---|---|---|---|
| 1/23 (4%) | 1/32 (3%) | 2/28 (7%) | 2/28 (7%) | 5/25 (20%) | 6/23 (26%) | 1/19 (5%) | 3/19 (16%) | 1/22 (5%) | 2/29 (7%) | 3/22 (14%) |

TABLE 14

Frequency of Gene Promoter Methylation in Colorectal Cancer Patients' Blood Methylation

| MGMT | P16 | RAR-β | RASSF1A | APC |
|---|---|---|---|---|
| 2/16 (13%) | 0/16 (0%) | 0/16 (0%) | 1/16 (6%) | 4/16 (25%) |

In this study LOH, for any one marker, was identified in 17 (52%) of 33 patients blood samples (Table 13) and promoter region hypermethylation at any marker was detected in 6 (38%) of 16 patients (Table 14). The combination of hypermethylation and LOH for assessing blood in those 16 patients evaluated using both techniques identified a greater number of patients with colorectal cancer, 15 (94%) of 16 as compared to either method alone: methylation 6 (38%) or LOH 11 (69%) of 16 patients (Table 15).

TABLE 15

Frequency of Methylation, LOH, and Their Combination in Colorectal Cancer Patients' Blood Assessed Using Both Assays

|  |  | Methylation | | Total |
|---|---|---|---|---|
|  |  | + | − | LOH |
| LOH | + | 2 | 9 | 11 |
|  | − | 4 | 1 | 5 |
| Total Methylation |  | 6 | 10 |  |

Detection of LOH and Methylation Markers in Primary Breast Cancer Tumors to Predict Metastasis to Lymph Nodes and Disease Outcome. Methylation PCR was carried out on primary tumors (151 patients) for the different markers. Patients were divided into those that had no metastasis in their sentinel lymph node (first tumor draining lymph node), occult or micrometastasis in their lymph nodes, or had palpable (clinically detectable) metastasis in their lymph nodes. Preliminary analysis demonstrated that methylation of specific markers in the primary tumor can predict the type of metastasis in the nodes. The results shown in Table 16 indicate that additional diagnostic data may be obtained from lymph node metastasis samples.

TABLE 16

Methylation Status of Primary Tumor and Lymph Node (LN) Metastasis (29 Pairs)

| Primary - LN met | APC | GSTP1 | RASSF1A | RAR-b | E-cad | TWIST* |
|---|---|---|---|---|---|---|
| M—M | 8 | 7 | 16 | 9 | 14 | 7 |
| M - U | 7 | 3 | 7 | 5 | 1 | 5 |
| U - M | 2 | 0 | 1 | 5 | 12 | 1 |
| U—U | 12 | 19 | 5 | 10 | 2 | 15 |

M stands for methylated and
U stands for unmethylated

Inventors believe that the same markers can be used to analyze blood (plasma/serum) and BM samples of melanoma patients.

REFERENCES

1. Abrams, H. L., Spiro, R. & Goldstein, N. Metastasis in carcinoma. *Cancer* 3, 74-85 (1950).
2. Lee, Y. T. Breast carcinoma: pattern of metastasis at autopsy. *J Surg Oncol* 23, 175-80 (1983).
3. Molino, A. et al. A comparative analysis of three different techniques for the detection of breast cancer cells in bone marrow. *Cancer* 67, 1033-1036 (1991).
4. Beiske, K. et al. Detection of bone marrow metastases in small cell lung cancer patients. Comparison of immunologic and morphologic methods. *Am J Pathol* 141, 531-8 (1992).
5. Osborne, M., Asina, S., Wong, G., Old, L. & Cote, R. Immunofluorescent monoclonal antibody detection of breast cancer in bone marrow: sensitivity in a model system. *Cancer Res* 49, 2510-2513 (1989).
6. Chaiwun, B. et al. Immunohistochemical detection of occult carcinoma in bone marrow and blood. *Diagn Oncol* 2, 267-276 (1992).
7. Rye, P., Hoifodt, H., Overli, G. & Fodstad, O. Immunobead filtration: a novel approach for the isolation and propagation of tumor cells. *Amer J Path* 150, 99-106 (1997).
8. Braun, S. et al. Micrometastatic breast cancer cells in bone marrow at primary surgery: Prognostic value in comparison with nodal status. *J Natl Cancer Inst* 90, 1099-1101 (1998).
9. Diel, I. J. et al. Micrometastatic breast cancer cells in bone marrow at primary surgery: prognostic value in comparison with nodal status. *J Natl Cancer Inst* 88, 1652-8. (1996).
10. Litle, V. R., Lockett, S. J. & Pallavicini, M. G. Genotype/phenotype analyses of low frequency tumor cells using computerize image microscopy. *Cytometry* 23, 344-9 (1996).
11. Moll, R., Franke, W. W., Schiller, D. L., Geiger, B. & Krepler, R. The catalog of human cytokeratins: patterns of expression in normal epithelia, tumors and cultured cells. *Cell* 31, 11-24 (1982).
12. Takita, K. et al. Correlation of loss of alleles on the short arms of chromosomes 11 and 17 with metastasis of primary breast cancer to lymph nodes. *Cancer Res* 52, 3914-7 (1992).
13. Hampl, M. et al. Loss of heterozygosity accumulation in primary breast carcinomas and additionally in corresponding distant metastases is associated with poor outcome. *Clin Cancer Res* 5, 1417-25. (1999).
14. Driouch, K. et al. Loss of heterozygosity on chromosome arm 16q in breast cancer metastases. *Genes Chromosomes Cancer* 19, 185-91. (1997).
15. Silva, J. M. et al. Abnormal frequencies of alleles in polymorphic markers of the 17q21 region is associated with breast cancer. *Cancer Lett* 138, 209-15 (1999).
16. Emi, M. et al. Allelic loss at 1p34, 13q12, 17p13.3, and 17q21.1 correlates with poor postoperative prognosis in breast cancer. *Genes Chromosomes Cancer* 26, 134-41 (1999).
17. Hirano, A. et al. Allelic losses of loci at 3p25.1, 8p22, 13q12, 17p13.3, and 22q13 correlate with postoperative recurrence in breast cancer. *Clin Cancer Res* 7, 876-82 (2001).
18. Anker, P. et al. K-ras mutations are found in DNA extracted from the plasma of patients with colorectal cancer. *Gastroenterology* 112, 1114-20 (1997).
19. Chen, X. et al. Detecting tumor-related alterations in plasma or serum DNA of patients diagnosed with breast cancer. *Clin Cancer Res* 5, 2297-303 (1999).
20. Chen, X. Q. et al. Microsatellite alterations in plasma DNA of small cell lung cancer patients. *Nat Med* 2, 1033-5 (1996).
21. Silva, J. M. et al. Presence of tumor DNA in plasma of breast cancer patients: clinicopathological correlations. *Cancer Res* 59, 3251-3256 (1999).
22. Shaw, J. A. et al. Microsatellite alterations plasma DNA of primary breast cancer patients. *Clin Cancer Res* 6, 1119-24 (2000).
23. Taback, B., Giuliano, A. E., Hansen, N. M. & Hoon, D. S. Microsatellite alterations detected in the serum of early stage breast cancer patients. *Ann N Y Acad Sci* 945, 22-30 (2001).
24. Taback, B. et al. Prognostic significance of circulating microsatellite markers in the plasma of melanoma patients. *Cancer Res* 61, 5723-5726 (2001).
25. Sanchez-Cespedes, M. et al. Detection of chromosome 3p alterations in serum DNA of non-small-cell lung cancer patients. *Ann Oncol* 9, 113-6 (1998).
26. Goessl, C. et al. Microsatellite analysis of plasma DNA from patients with clear cell renal carcinoma. *Cancer Res* 58, 4728-32 (1998).
27. Fujiwara, Y. et al. Plasma DNA microsatellites as tumor-specific markers and indicators of tumor progression in melanoma patients. *Cancer Res* 59, 1567-1571 (1999).
28. Hibi, K. et al. Molecular detection of genetic alterations in the serum of colorectal cancer patients. *Cancer Res* 58, 1405-1407 (1998).
29. Kopreski, M. S. et al. Detection of mutant K-ras DNA in plasma or serum of patients with colorectal cancer. *Br J Cancer* 76, 1293-9 (1997).
30. Mayall, F., Fairweather, S., Wilkins, R., Chang, B. & Nicholls, R. Microsatellite abnormalities in plasma of patients with breast carcinoma: concordance with the primary tumour. *J Clin Pathol* 52, 363-6 (1999).
31. Nawroz, H., Koch, W., Anker, P., Stroun, M. & Sidransky, D. Microsatellite alterations in serum DNA of head and neck cancer patients. *Nat Med* 2, 1035-1037 1996).
32. Stroun, M., Anker, P., Lyautey, J., Lederrey, C. & Maurice, P. A. Isolation and characterization of DNA from the plasma of cancer patients. *Eur J Cancer Clin Oncol* 23, 707-12 (1987).

33. Mansi, J. L. et al. Bone marrow micrometastases in primary breast cancer: prognostic significance after 6 years' follow-up. *Eur J Cancer* 27, 1552-5. (1991).
34. Berger, U. et al. The relationship between micrometastases in the bone marrow, histopathologic features of the primary tumor in breast cancer and prognosis. *Am J Clin Pathol* 90, 1-6 (1988).
35. Cote, R., Rosen, P., Lesser, M., Old, L. & Osborne, M. Prediction of early relapse in patients with operable breast cancer by detection of occult bone marrow micrometastasis. *J Clin Oncol* 9, 1749-1756 (1991).
36. Dearnaley, D. P., Ormerod, M. G. & Sloane, J. P. Micrometastases in breast cancer: long-term follow-up of the first patient cohort. *Eur J Cancer* 27, 236-9 (1991).
37. Harbeck, N., Untch, M., Pache, L. & Eiermann, W. Tumour cell detection in the bone marrow of breast cancer patients at primary therapy: results of a 3-year median follow-up. *Br J Cancer* 69, 566-71 (1994).
38. Braun, S. et al. Cytokeratin-positive cells in the bone marrow and survival of patients with stage I, II, or III breast cancer. *N Engl J Med* 342, 525-33 (2000).
39. Zippelius, A. et al. Limitations of reverse-transcriptase polymerase chain reaction analysis for the detection of micrometastatic epithelial cancer cells in bone marrow. *Journal of Clinical Oncology* 15, 2701-2708 (1997).
40. Bostick, P. J. et al. Limitations of specific reverse-transcriptase polymerase chain reaction markers in the detection of metastases in the lymph nodes and blood of breast cancer patients. *J Clin Oncol* 16, 2632-40 (1998).
41. Ko, Y. et al. Limitations of the reverse transcription-polymerase chain reaction method for the detection of carcinoembryonic antigen-positive tumor cells in peripheral blood. *Clin Cancer Res* 4, 2141-6 (1998).
42. Jung, R. et al. Specificity of reverse transcriptase polymerase chain reaction assays designed for the detection of circulating cancer cells is influenced by cytokines in vivo and in vitro. *Br J Cancer* 78, 1194-8 (1998).
43. O'Connell, P. et al. Loss of heterozygosity at D14S62 and metastatic potential of breast cancer. *J Natl Cancer Inst* 91, 1391-7 (1999).
44. Jones, P. A. and Baylin, S. B. The fundamental role of epigenetic events in cancer. *Nat Rev Genet*, 3: 415-428, 2002.
45. Baylin, S. B. and Herman, J. G. DNA hypermethylation in tumorigenesis: epigenetics joins genetics. *Trends Genet*, 16: 168-174, 2000.
46. Herman, J. G., Graff, J. R., Myohanen, S., Nelkin, B. D., and Baylin, S. B. Methylation-specific PCR: a novel PCR assay for methylation status of CpG islands. *Proc Natl Acad Sci U S A*, 93: 9821-9826, 1996.
47. Esteller, M., Corn, P. G., Baylin, S. B., and Herman, J. G. A gene hypermethylation profile of human cancer. *Cancer Res*, 61: 3225-3229, 2001.
48. Sidransky, D. Emerging molecular markers of cancer. *Nat Rev Cancer*, 2: 210-219, 2002.
49. Baylin, S. and Bestor, T. H. Altered methylation patterns in cancer cell genomes: cause or consequence? *Cancer Cell*, 1: 299-305, 2002.
50. Costello, J. F., Fruhwald, M. C., Smiraglia, D. J., Rush, L. J., Robertson, G. P., Gao, X., Wright, F. A., Feramisco, J. D., Peltomaki, P., Lang, J. C., Schuller, D. E., Yu, L., Bloomfield, C. D., Caligiuri, M. A., Yates, A., Nishikawa, R., Su Huang, H., Petrelli, N. J., Zhang, X., O'Dorisio, M. S., Held, W. A., Cavenee, W. K., and Plass, C. Aberrant CpG-island methylation has non-random and tumour-type-specific patterns. *Nat Genet*, 24: 132-138, 2000.
51. Fujimoto, A., Morita, R., Hatta, N., Takehara, K., and Takata, M. p16INK4a inactivation is not frequent in uncultured sporadic primary cutaneous melanoma. *Oncogene*, 18: 2527-2532, 1999.
52. Merbs, S. L. and Sidransky, D. Analysis of p16 (CDKN2/MTS-1/INK4A) alterations in primary sporadic uveal melanoma. *Invest Ophthalmol Vis Sci*, 40: 779-783, 1999.
53. Christmann, M., Pick, M., Lage, H., Schadendorf, D., and Kaina, B. Acquired resistance of melanoma cells to the antineoplastic agent fotemustine is caused by reactivation of the DNA repair gene MGMT. *Int J Cancer*, 92: 123-129, 2001.
54. Dammann, R., Li, C., Yoon, J. H., Chin, P. L., Bates, S., and Pfeifer, G. P. Epigenetic inactivation of a RAS association domain family protein from the lung tumour suppressor locus 3p21.3. *Nat Genet*, 25: 315-319, 2000.
55. Dammann, R., Yang, G., and Pfeifer, G. P. Hypermethylation of the cpG island of Ras association domain family 1A (RASSF1A), a putative tumor suppressor gene from the 3p21.3 locus, occurs in a large percentage of human breast cancers. *Cancer Res*, 61: 3105-3109, 2001.
56. Sekido, Y., Ahmadian, M., Wistuba, I I, Latif, F., Bader, S., Wei, M. H., Duh, F. M., Gazdar, A. F., Lerman, M. I., and Minna, J. D. Cloning of a breast cancer homozygous deletion junction narrows the region of search for a 3p21.3 tumor suppressor gene. *Oncogene*, 16: 3151-3157, 1998.
57. Burbee, D. G., Forgacs, E., Zochbauer-Muller, S., Shivakumar, L., Fong, K., Gao, B., Randle, D., Kondo, M., Virmani, A., Bader, S., Sekido, Y., Latif, F., Milchgrub, S., Toyooka, S., Gazdar, A. F., Lerman, M. I., Zabarovsky, E., White, M., and Minna, J. D. Epigenetic inactivation of RASSF1A in lung and breast cancers and malignant phenotype suppression. *J Natl Cancer Inst*, 93: 691-699, 2001.
58. Kuzmin, I., Gillespie, J. W., Protopopov, A., Geil, L., Dreijerink, K., Yang, Y., Vocke, C. D., Duh, F. M., Zabarovsky, E., Minna, J. D., Rhim, J. S., Emmert-Buck, M. R., Linehan, W. M., and Lerman, M. I. The RASSF1A tumor suppressor gene is inactivated in prostate tumors and suppresses growth of prostate carcinoma cells. *Cancer Res*, 62: 3498-3502, 2002.
59. Lo, K. W., Kwong, J., Hui, A. B., Chan, S. Y., To, K. F., Chan, A. S., Chow, L. S., Teo, P. M., Johnson, P. J., and Huang, D. P. High frequency of promoter hypermethylation of RASSF1A in nasopharyngeal carcinoma. *Cancer Res*, 61: 3877-3881, 2001.
60. Clark, S. J., Harrison, J., Paul, C. L., and Frommer, M. High sensitivity mapping of methylated cytosines. *Nucleic Acids Res*, 22: 2990-2997, 1994.
61. Grunau, C., Clark, S. J., and Rosenthal, A. Bisulfite genomic sequencing: systematic investigation of critical experimental parameters. Nucleic Acids Res, 29: E65-65, 2001.
62. Baylin, S. and Bestor, T. H. Altered methylation patterns in cancer cell genomes: cause or consequence? *Cancer Cell*, 1: 299-305, 2002.
63. Baylin, S. B., Belinsky, S. A., and Herman, J. G. Aberrant methylation of gene promoters in cancer—concepts, misconcepts, and promise. *J Natl Cancer Inst*, 92: 1460-1461, 2000.
64. Belinsky, S. A., Nikula, K. J., Palmisano, W. A., Michels, R., Saccomanno, G., Gabrielson, E., Baylin, S. B., and Herman, J. G. Aberrant methylation of p16 (INK4a) is an early event in lung cancer and a potential biomarker for early diagnosis. *Proc Natl Acad Sci U S A*, 95: 11891-11896, 1998.

65. Herman, J. G., Jen, J., Merlo, A., and Baylin, S. B. Hypermethylation-associated inactivation indicates a tumor suppressor role for p15INK4B. *Cancer Res*, 56: 722-727, 1996.

66. Esteller, M., Corn, P. G., Baylin, S. B., and Herman, J. G. A gene hypermethylation profile of human cancer. *Cancer Res*, 61: 3225-3229, 2001.

67. Virmani, A. K., Rathi, A., Zochbauer-Muller, S., Sacchi, N., Fukuyama, Y., Bryant, D., Maitra, A., Heda, S., Fong, K. M., Thunnissen, F., Minna, J. D., and Gazdar, A. F. Promoter methylation and silencing of the retinoic acid receptor-beta gene in lung carcinomas. *J Natl Cancer Inst*, 92: 1303-1307, 2000.

68. Esteller, M., Garcia-Foncillas, J., Andion, E., Goodman, S. N., Hidalgo, O. F., Vanaclocha, V., Baylin, S. B., and Herman, J. G. Inactivation of the DNA-repair gene MGMT and the clinical response of gliomas to alkylating agents. *N Engl J Med*, 343: 1350-1354, 2000.

69. Esteller, M., Hamilton, S. R., Burger, P. C., Baylin, S. B., and Herman, J. G. Inactivation of the DNA repair gene O6-methylguanine-DNA methyltransferase by promoter hypermethylation is a common event in primary human neoplasia. *Cancer Res*, 59: 793-797, 1999.

70. Esteller, M., Sanchez-Cespedes, M., Rosell, R., Sidransky, D., Baylin, S. B., and Herman, J. G. Detection of aberrant promoter hypermethylation of tumor suppressor genes in serum DNA from non-small cell lung cancer patients. *Cancer Res*, 59: 67-70, 1999.

71. Esteller, M., Toyota, M., Sanchez-Cespedes, M., Capella, G., Peinado, M. A., Watkins, D. N., Issa, J. P., Sidransky, D., Baylin, S. B., and Herman, J. G. Inactivation of the DNA repair gene O6-methylguanine-DNA methyltransferase by promoter hypermethylation is associated with G to A mutations in K-ras in colorectal tumorigenesis. Cancer Res, 60: 2368-2371, 2000.

72. Lo, K. W., Kwong, J., Hui, A. B., Chan, S. Y., To, K. F., Chan, A. S., Chow, L. S., Teo, P. M., Johnson, P. J., and Huang, D. P. High frequency of promoter hypermethylation of RASSF1A in nasopharyngeal carcinoma. *Cancer Res*, 61: 3877-3881, 2001.

73. Jones, P. A. and Baylin, S. B. The fundamental role of epigenetic events in cancer. *Nat Rev Genet*, 3: 415-428, 2002.

74. Nakayama, T., Watanabe, M., Yamanaka, M., Hirokawa, Y., Suzuki, H., Ito, H., Yatani, R., and Shiraishi, T. The role of epigenetic modifications in retinoic acid receptor beta2 gene expression in human prostate cancers. *Lab Invest*, 81: 1049-1057, 2001.

75. Dammann, R., Yang, G., and Pfeifer, G. P. Hypermethylation of the cpG island of Ras association domain family 1A (RASSF1A), a putative tumor suppressor gene from the 3p21.3 locus, occurs in a large percentage of human breast cancers. *Cancer Res*, 61: 3105-3109, 2001.

76. Dammann, R., Li, C., Yoon, J. H., Chin, P. L., Bates, S., and Pfeifer, G. P. Epigenetic inactivation of a RAS association domain family protein from the lung tumour suppressor locus 3p21.3. *Nat Genet*, 25: 315-319, 2000.

77. Harada, K., Toyooka, S., Maitra, A., Maruyama, R., Toyooka, K. O., Timmons, C. F., Tomlinson, G. E., Mastrangelo, D., Hay, R. J., Minna, J. D., and Gazdar, A. F. Aberrant promoter methylation and silencing of the RASSF1A gene in pediatric tumors and cell lines. *Oncogene*, 21: 4345-4349, 2002.

78. Burbee, D. G., Forgacs, E., Zochbauer-Muller, S., Shivakumar, L., Fong, K., Gao, B., Randle, D., Kondo, M., Virmani, A., Bader, S., Sekido, Y., Latif, F., Milchgrub, S., Toyooka, S., Gazdar, A. F., Lerman, M. I., Zabarovsky, E., White, M., and Minna, J. D. Epigenetic inactivation of RASSF1A in lung and breast cancers and malignant phenotype suppression. *J Natl Cancer Inst*, 93: 691-699, 2001.

Baylin, S. B. & Herman, J. G. (2000). *Trends Genet*, 16, 168-174.

Bostick, P. J., Morton, D. L., Turner, R. R., Huynh, K. T., Wang, H. J., Elashoff, R., Essner, R. & Hoon, D. S. (1999). *J Clin Oncol*, 17, 3238-3244.

Chen, C. M., Chen, H. L., Hsiau, T. H., Hsiau, A. H., Shi, H., Brock, G. J., Wei, S. H., Caldwell, C. W., Yan, P. S. & Huang, T. H. (2003). *Am J Pathol*, 163, 37-45.

Christmann, M., Pick, M., Lage, H., Schadendorf, D. & Kaina, B. (2001). *Int J Cancer*, 92, 123-129.

Dammann, R., Li, C., Yoon, J. H., Chin, P. L., Bates, S. & Pfeifer, G. P. (2000). *Nat Genet*, 25, 315-319.

Dammann, R., Yang, G. & Pfeifer, G. P. (2001). *Cancer Res*, 61, 3105-3109.

Davies, H., Bignell, G. R., Cox, C., Stephens, P., Edkins, S., Clegg, S., Teague, J., Woffendin, H., Garnett, M. J., Bottomley, W., Davis, N., Dicks, E., Ewing, R., Floyd, Y., Gray, K., Hall, S., Hawes, R., Hughes, J., Kosmidou, V., Menzies, A., Mould, C., Parker, A., Stevens, C., Watt, S., Hooper, S., Wilson, R., Jayatilake, H., Gusterson, B. A., Cooper, C., Shipley, J., Hargrave, D., Pritchard-Jones, K., Maitland, N., Chenevix-Trench, G., Riggins, G. J., Bigner, D. D., Palmieri, G., Cossu, A., Flanagan, A., Nicholson, A., Ho, J. W., Leung, S. Y., Yuen, S. T., Weber, B. L., Seigler, H. F., Darrow, T. L., Paterson, H., Marais, R., Marshall, C. J., Wooster, R., Stratton, M. R. & Futreal, P. A. (2002). *Nature*, 417, 949-954.

Demary, K., Wong, L., Liou, J. S., Faller, D. V. & Spanjaard, R. A. (2001). *Endocrinology*, 142, 2600-2605.

Eads, C. A., Danenberg, K. D., Kawakami, K., Saltz, L. B., Danenberg, P. V. & Laird, P. W. (1999). *Cancer Res*, 59, 2302-2306.

Esteller, M., Corn, P. G., Baylin, S. B. & Herman, J. G. (2001). *Cancer Res*, 61, 3225-3229.

Esteller, M., Hamilton, S. R., Burger, P. C., Baylin, S. B. & Herman, J. G. (1999). *Cancer Res*, 59, 793-797.

Esteller, M. & Herman, J. G. (2002). *J Pathol*, 196, 1-7.

Evron, E., Dooley, W. C., Umbricht, C. B., Rosenthal, D., Sacchi, N., Gabrielson, E., Soito, A. B., Hung, D. T., Ljung, B., Davidson, N. E. & Sukumar, S. (2001). *Lancet*, 357, 1335-1336.

Fujiwara, Y., Chi, D. D., Wang, H., Keleman, P., Morton, D. L., Turner, R. & Hoon, D. S. (1999). *Cancer Res*, 59, 1567-1571.

Goessl, C., Krause, H., Muller, M., Heicappell, R., Schrader, M., Sachsinger, J. & Miller, K. (2000). *Cancer Res*, 60, 5941-5945.

Harden, S. V., Tokumaru, Y., Westra, W. H., Goodman, S., Ahrendt, S. A., Yang, S. C. & Sidransky, D. (2003). *Clin Cancer Res*, 9, 1370-1375.

Jeronimo, C., Usadel, H., Henrique, R., Oliveira, J., Lopes, C., Nelson, W. G. & Sidransky, D. (2001). *J Natl Cancer Inst*, 93, 1747-1752.

Johnson, P. J. & Lo, Y. M. (2002). *Clin Chem*, 48, 1186-1193.

Jones, P. A. & Baylin, S. B. (2002). *Nat Rev Genet*, 3, 415-428.

Kurie, J. M., Lotan, R., Lee, J. J., Lee, J. S., Morice, R. C., Liu, D. D., Xu, X. C., Khuri, F. R., Ro, J. Y., Hittelman, W. N., Walsh, G. L., Roth, J. A., Minna, J. D. & Hong, W. K. (2003). *J Natl Cancer Inst*, 95, 206-214.

Lo, K. W., Kwong, J., Hui, A. B., Chan, S. Y., To, K. F., Chan, A. S., Chow, L. S., Teo, P. M., Johnson, P. J. & Huang, D. P. (2001). *Cancer Res*, 61, 3877-3881.

Mangelsdorf, D. J. & Evans, R. M. (1995). *Cell*, 83, 841-850.

Maruyama, R., Toyooka, S., Toyooka, K. O., Harada, K., Virmani, A. K., Zochbauer-Muller, S., Farinas, A. J., Vakar-Lopez, F., Minna, J. D., Sagalowsky, A., Czerniak, B. & Gazdar, A. F. (2001). *Cancer Res,* 61, 8659-8663.

Paz, M. F., Fraga, M. F., Avila, S., Guo, M., Pollan, M., Herman, J. G. & Esteller, M. (2003). *Cancer Res,* 63, 1114-1121.

Pfeifer, G. P., Yoon, J. H., Liu, L., Tommasi, S., Wilczynski, S. P. & Dammann, R. (2002). *Biol Chem,* 383, 907-914.

Rosas, S. L., Koch, W., da Costa Carvalho, M. G., Wu, L., Califano, J., Westra, W., Jen, J. & Sidransky, D. (2001). *Cancer Res,* 61, 939-942.

Shi, H., Wei, S. H., Leu, Y. W., Rahmatpanah, F., Liu, J. C., Yan, P. S., Nephew, K. P. & Huang, T. H. (2003). *Cancer Res,* 63, 2164-2171.

Sidransky, D. (2002). *Nat Rev Cancer,* 2, 210-219.

Sirchia, S. M., Ren, M., Pili, R., Sironi, E., Somenzi, G., Ghidoni, R., Toma, S., Nicolo, G. & Sacchi, N. (2002). *Cancer Res,* 62, 2455-2461.

Smiraglia, D. J., Rush, L. J., Fruhwald, M. C., Dai, Z., Held, W. A., Costello, J. F., Lang, J. C., Eng, C., Li, B., Wright, F. A., Caligiuri, M. A. & Plass, C. (2001). *Hum Mol Genet,* 10, 1413-1419.

Spanjaard, R. A., Ikeda, M., Lee, P. J., Charpentier, B., Chin, W. W. & Eberlein, T. J. (1997). *J Biol Chem,* 272, 18990-18999.

Spugnardi, M., Tommasi, S., Dammann, R., Pfeifer, G. P. & Hoon, D. S. (2003). *Cancer Res,* 63, 1639-1643.

Taback, B., Fujiwara, Y., Wang, H. J., Foshag, L. J., Morton, D. L. & Hoon, D. S. (2001). *Cancer Res,* 61, 5723-5726.

Takeuchi, H., Kuo, C., Morton, D. L., Wang, H. J. & Hoon, D. S. (2003). *Cancer Res,* 63, 441-448.

Toyooka, S., Maruyama, R., Toyooka, K. O., McLerran, D., Feng, Z., Fukuyama, Y., Virmani, A. K., Zochbauer-Muller, S., Tsukuda, K., Sugio, K., Shimizu, N., Shimizu, K., Lee, H., Chen, C. Y., Fong, K. M., Gilcrease, M., Roth, J. A., Minna, J. D. & Gazdar, A. F. (2003). *Int J Cancer,* 103, 153-160.

Ueki, T., Toyota, M., Sohn, T., Yeo, C. J., Issa, J. P., Hruban, R. H. & Goggins, M. (2000). *Cancer Res,* 60, 1835-1839.

Usadel, H., Brabender, J., Danenberg, K. D., Jeronimo, C., Harden, S., Engles, J., Danenberg, P. V., Yang, S. & Sidransky, D. (2002). *Cancer Res,* 62, 371-375.

Widschwendter, M., Berger, J., Hermann, M., Muller, H. M., Amberger, A., Zeschnigk, M., Widschwendter, A., Abendstein, B., Zeimet, A. G., Daxenbichler, G. & Marth, C. (2000). *J Natl Cancer Inst,* 92, 826-832.

Widschwendter, M. & Jones, P. A. (2002). *Oncogene,* 21, 5462-5482.

Zochbauer-Muller, S., Fong, K. M., Virmani, A. K., Geradts, J., Gazdar, A. F. & Minna, J. D. (2001). *Cancer Res,* 61, 249-255.

While the foregoing has been described in considerable detail and in terms of preferred embodiments, these are not to be construed as limitations on the disclosure or claims to follow. Modifications and changes that are within the purview of those skilled in the art are intended to fall within the scope of the following claims. All literatures cited herein are incorporated by reference in their entirety.

---

What is claimed is:

1. A method of detecting DNA markers in a sample, comprising:
   Providing a cell-free bone marrow sample from a subject; and
   detecting one or more DNA markers in the sample, wherein the DNA markers are indicative of LOH or DNA hypermethylation, or the DNA markers are indicative of DNA mutation in KRAS or BRAF gene.

2. The method of claim 1, wherein the DNA markers are in the 1p, 3p, 6p, 6q, 8p, 10q, 11q, 14q, 16q, or 17p region.

3. The method of claim 1, wherein the DNA markers include D1S228, D8S321, D4S175, D4S1586, D5S299, D8S133, D8S261, D8S262, D8S264, D9S171, D10S197, D10S591, D10S532, D14S51, D14S62, D15S127, D16S421, D16S422, D17S796, D17S849, D17S855, D18S58, D18S61, or D18S70.

4. The method of claim 1, wherein the DNA markers are indicative of hypermethylation in RASSF1A, MGMT, GSTP1, RAR-β, TWIST, APC, DAPK, P16, or Cyclin D2 promoter.

5. A method of detecting cancer, comprising
   providing a cell-free bone marrow sample from a subject; and
   detecting one or more DNA markers in the sample, wherein LOH or hypermethylation of the markers is indicative of cancer in the subject, or wherein the markers include KRAS or BRAF, and mutation of the markers is indicative of cancer in the subject.

6. The method of claim 5, wherein the cancer is melanoma, neuroblastoma, colorectal, breast, or prostate cancer.

7. A method of staging cancer, comprising
   providing a cell-free bone marrow sample from a subject suffering from cancer; and
   detecting one or more DNA markers in the sample, wherein LOH, hypermethylation, or mutation of the markers is indicative of an advanced stage of the cancer in the subject.

8. The method of claim 7, wherein the cancer is melanoma, neuroblastoma, colorectal, breast, or prostate cancer.

9. A method of prognosing cancer, comprising
   providing a cell-free bone marrow sample from a subject suffering from cancer; and
   detecting one or more DNA markers in the sample, wherein LOH, hypermethylation, or mutation of the markers is indicative of a poor prognosis of the cancer in the subject.

10. The method of claim 9, wherein the cancer is melanoma, neuroblastoma, colorectal, breast, or prostate cancer.

11. A method of detecting LOH and DNA hypermethylation, comprising
    providing a cell-free marrow sample from a subject; and
    detecting a combination of LOH and DNA hypermethylation in the sample.

12. A method of detecting LOH and DNA hypermethylation, comprising
    providing a cell-free bone marrow sample from a subject; and
    detecting a combination of LOH and DNA hypermethylation in the sample, wherein the LOH is indicated by one or more DNA markers that include D1S228, D8S321, D4S175, D4S1586, D5S299, D8S133, D8S261, D8S262, D8S264, D9S171, D10S591, D10S532, D14S51, D14S62, D15S127, D16S421, D16S422, D17S796, D17S849, D17S855, D18S58, D18S61, or D18S70.

13. A method of detecting LOH and DNA hypermethylation, comprising
    providing a cell-free bone marrow sample from a subject; and
    detecting a combination of LOH and DNA hypermethylation in the sample, wherein the DNA hypermethylation is detected in RASSF1A, MGMT, GSTP1, RAR-β, TWIST, APC, DAPK, or Cyclin D2 promoter.

14. A method of detecting cancer, comprising
    providing a cell-free bone marrow sample from a subject; and
    detecting one or more DNA markers in the sample, wherein a combination of LOH and hypermethylation of the markers is indicative of cancer in the subject.

15. A method of detecting cancer, comprising
    providing a cell-free bone marrow sample from a subject; and
    detecting one or more DNA markers in the sample, wherein a combination of LOH and hypermethylation of the markers is indicative of melanoma, neuroblastoma, colorectal, or prostate cancer in the subject.

16. A method of staging cancer, comprising
    providing a cell-free bone marrow sample from a subject suffering from cancer; and
    detecting one or more DNA markers in the sample, wherein a combination of LOH and hypermethylation of the markers is indicative of an advanced stage of the cancer in the subject.

17. The method of claim 16, wherein the cancer is melanoma, neuroblastoma, colorectal, breast, or prostate cancer.

18. A method of prognosing cancer, comprising
    providing a cell-free bone marrow sample from a subject suffering from cancer; and
    detecting one or more DNA markers in the sample, wherein a combination of LOH and hypermethylation of the markers is indicative of a poor prognosis of the cancer in the subject.

19. The method of claim 18, wherein the cancer is melanoma, neuroblastoma, colorectal, breast, or prostate cancer.

* * * * *